US011813636B2

(12) United States Patent
Bakus et al.

(10) Patent No.: US 11,813,636 B2
(45) Date of Patent: Nov. 14, 2023

(54) DEVICES, SYSTEMS, AND METHODS FOR REDUCING MICROBIAL LOAD DURING PRODUCT COATING

(71) Applicant: Apeel Technology, Inc., Goleta, CA (US)

(72) Inventors: Ronald C. Bakus, Goleta, CA (US); Matthew Kahlscheuer, Goleta, CA (US); Gregory Faust, Goleta, CA (US); Louis Perez, Goleta, CA (US); Anuj Purohit, Goleta, CA (US); Krishnan Chari, Goleta, CA (US); Benjamin Gordon, Goleta, CA (US); Nicholas Feringa, Goleta, CA (US); Doug Gotthard, Goleta, CA (US)

(73) Assignee: Apeel Technology, Inc., Goleta, CA (US)

( * ) Notice: Subject to any disclaimer, the term of this patent is extended or adjusted under 35 U.S.C. 154(b) by 235 days.

(21) Appl. No.: 17/696,417

(22) Filed: Mar. 16, 2022

(65) Prior Publication Data

US 2022/0297153 A1 Sep. 22, 2022

Related U.S. Application Data

(60) Provisional application No. 63/162,293, filed on Mar. 17, 2021.

(51) Int. Cl.
*C09D 5/14* (2006.01)
*A61L 2/10* (2006.01)
(Continued)

(52) U.S. Cl.
CPC ................ *B05C 1/02* (2013.01); *A23B 7/015* (2013.01); *A23B 7/16* (2013.01); *A23L 3/28* (2013.01);
(Continued)

(58) Field of Classification Search
CPC .......... A61L 2/10; A61L 2/18; A61L 2101/30; B05C 1/02; A23P 20/18; A23B 7/16;
(Continued)

(56) References Cited

U.S. PATENT DOCUMENTS

| | | | |
|---|---|---|---|
| 1,975,991 | A | 10/1934 | Tranin et al. |
| 6,033,705 | A | 3/2000 | Isaacs |

(Continued)

FOREIGN PATENT DOCUMENTS

| | | |
|---|---|---|
| CN | 205731997 | 11/2016 |
| CN | 208080509 | 11/2018 |
| EP | 2145678 | 1/2010 |
| GB | 2388764 | 11/2003 |
| IN | 2020041038516 | 9/2020 |
| KR | 20110130004 | 12/2011 |
| WO | 2004/004470 | 1/2004 |
| WO | 2020/023319 | 1/2020 |

OTHER PUBLICATIONS

International Search Report and Written Opinion in International Appln. No. PCT/US2022/020550, dated Aug. 16, 2022, 21 pages.

*Primary Examiner* — Sean E Conley
(74) *Attorney, Agent, or Firm* — Fish & Richardson P.C.

(57) ABSTRACT

A treatment system, including a conveyor bed configured to transport a plurality of products; a brushing device located along the conveyor bed and having one or more brushes that include a first antimicrobial compound; a surface treatment device including a lamp configured to emit light of a peak wavelength directed toward a portion of the conveyor bed; and a coating device configured to deliver a coating mixture onto the plurality of products on the conveyor bed.

16 Claims, 14 Drawing Sheets

(51) Int. Cl.

| | |
|---|---|
| ***A61L 2/18*** | (2006.01) |
| ***B05D 3/06*** | (2006.01) |
| ***A61L 101/30*** | (2006.01) |
| ***B05C 1/02*** | (2006.01) |
| ***B05C 11/10*** | (2006.01) |
| ***A23B 7/015*** | (2006.01) |
| ***A23B 7/16*** | (2006.01) |
| ***A23L 3/28*** | (2006.01) |
| ***A23P 20/18*** | (2016.01) |

(52) U.S. Cl.
CPC ................ *A23P 20/18* (2016.08); *A61L 2/10* (2013.01); *A61L 2/18* (2013.01); *B05C 11/10* (2013.01); *B05D 3/062* (2013.01); *C09D 5/14* (2013.01); *A61L 2101/30* (2020.08)

(58) Field of Classification Search
CPC .. A23B 7/015; A23L 3/28; C09D 5/14; B05D 3/062
See application file for complete search history.

(56) References Cited

U.S. PATENT DOCUMENTS

| | | | |
|---|---|---|---|
| 6,150,663 | A | 11/2000 | Rosenthal |
| 6,964,787 | B2 | 11/2005 | Swart et al. |
| 2004/0052702 | A1 | 3/2004 | Shuman et al. |
| 2011/0097370 | A1 | 4/2011 | Wang et al. |

DEVICES, SYSTEMS, AND METHODS FOR REDUCING MICROBIAL LOAD DURING PRODUCT COATING

CROSS-REFERENCE TO RELATED APPLICATIONS

This application claims the benefit of priority to U.S. Patent Application Ser. No. 63/162,293, filed on Mar. 17, 2021, the entire contents of which are hereby incorporated by reference.

TECHNICAL FIELD

This document describes devices, systems, and methods related to reduction of microbial load of products, such as devices, systems, and methods for applying antimicrobial processes during treatment of perishable products.

BACKGROUND

Common products, such as food products, agricultural products, and fresh produce, are susceptible to microbial contamination when exposed to the environment during harvest, packaging, or transport. These microbial stressors, such as bacteria, fungi, viruses, and/or pests, can infest and decompose the agricultural products and present downstream contamination concerns. For example, a single piece of contaminated agricultural product in the process of handling and distribution can contaminate other agricultural products with microbes, either by direct contact or contaminating an intermediate surface or media which then transfers the contamination onto other agricultural product.

SUMMARY

Reducing the number and type of microorganisms contaminating agricultural products, e.g., the microbial load, presents an industry-wide challenge, particularly for common human pathogens responsible for foodborne illness such as *Escherichia coli, Listeria monocytogenes*, and *Salmonella*. Incorporation of sanitization steps of microbial removal, such as brushing and washing, or microbial deactivation, e.g., sterilization can reduce microbial loading on products, such as fruit and vegetables.

Various embodiments described herein include one or more mechanisms that independently reduce the microbial load of agricultural products in a product treatment system. Some embodiments optionally include three or more treatments that reduce the microbial load on product surfaces, and/or prevent the transfer of contaminants between product surfaces. Briefly, an example treatment system optionally treats agricultural products through a brushing system to remove microbe-laden particulates, coating the products in a heated freshness-preserving material, and exposing surfaces to UVC light to neutralize microbial load.

In some example embodiments, a brushing mechanism includes bristles constructed, co-blended, impregnated, and/or coated with antimicrobial compounds or elements. Such compounds can include metallic nanoparticles, oxides, antimicrobials, and/or other compounds which inhibit or reduce microbial populations. The bristles agitate against the product surface removing microbes or microbe-laden particulates from the product surface. The microbes clinging to the bristles, or the liquid on the bristles, following removal are exposed to the antimicrobial compounds or elements, reducing the microbial activity on the bristles or in the liquid, and reducing transfer of microbes removed from a first product to subsequent products (e.g., prior to brush line decontamination).

In some example embodiments, a coating device dispenses heated coating mixture onto product surfaces. For example, the coating device can include a heating element and controller to heat the coating material to a predetermined elevated temperature sufficient to provide an antimicrobial effect. The heated coating material neutralizes microbes that may be present in the coating mixture, and/or on the product surface, via thermal inactivation.

In some example embodiments, a UV mechanism exposes the agricultural product or coating mixture to ultraviolet radiation, de-activating and reducing the microbial load on the product surface or in the coating mixture. For example, UVC radiation can selectively inactivate microorganisms while preserving the cellular components of the products. The UV mechanism can optionally include tumbling or otherwise manipulating the products to more uniformly expose product surfaces to the UV radiation.

Some embodiments of the devices, systems, and techniques described herein may provide one or more of the following advantages. First, some embodiments described herein facilitate removal of microbe-carrying particulates or microbes from product surfaces and reduce microbe transfer onto surfaces of other products (e.g., those subsequently passing through a treatment system). For example, the system may include brushes having antimicrobial compounds or elements that deactivate microbes. Such features can prevent cross contamination to other products processed with the system, reducing overall microbial content within the system and decreasing a likelihood of significant microbial content existing on treated products.

Second, various example embodiments can promote deactivation of microbial load present on product surfaces through thermal transfer. For example, application of a heated coating solution before application to the product deactivates microbes present both in the water-based coating and on the product that receives the coating. In some optional embodiments, heating the coating mixture can increase solute homogeneity in the solution and promote effective wetting, furthering the effectiveness of the coating process in reducing microbial content and extending the shelf-life of the coated product.

Third, various example embodiments can sanitize or otherwise reduce microbial load on product surfaces with limited or no mechanical contact of the product. For example, controlled exposure to ultraviolet light can reduce microbial load on product surfaces (e.g., by damaging microbial nucleic acids). The microbial content on product surfaces can be directly neutralized, promoting reduced microbial loading and limiting transfer of microbial content between products.

Fourth, various techniques can be used in combination (e.g., sequentially treating products in a treatment system) to enhance the overall effectiveness of reducing antimicrobial loading. For example, antimicrobial brushes, coating materials (e.g., heated coatings), and/or UV radiation, can be used in combination. In some embodiments, such techniques facilitate antimicrobial treatment in a relatively small footprint, without requiring extended floor space in a treatment facility.

Fifth, some embodiments described herein include techniques that complement one another to result in a greater reduction of microbial load when used together, as compared to the additive effect of each technique. As one example, a coating material (e.g., heated coating material)

can include antimicrobial compounds or elements that are activated or have enhanced antimicrobial characteristics by exposure to UV light and/or elevated temperature. Such techniques can enhance microbial load reduction during treatment, and promote long-term protection from additional contamination by foreign matter subsequently deposited on the protective coating. Moreover, exposure to ultraviolet light and/or a coating material can be enhanced by first removing any particulate or other matter from the product surface, for example.

Sixth, in some embodiments, the coating mixture can be formulated with additional antimicrobial compounds or elements to provide desired coating characteristics on the product that extend shelf-life and reduce microbial load present on product surfaces during the life of the product. The protective coating extends product shelf life thereby decreasing waste due to freshness losses. The protective coating additionally reduces moisture loss of the product increasing product freshness and appeal (e.g., when displayed to a consumer).

As additional description to the embodiments described below, the present disclosure describes the following embodiments.

Embodiment 1 is a treatment system, including a conveyor bed configured to transport a plurality of products; a brushing device located along the conveyor bed and having one or more brushes that include a first antimicrobial compound; a surface treatment device including a lamp configured to emit light of a peak wavelength directed toward a portion of the conveyor bed; and a coating device configured to deliver a coating mixture onto the plurality of products on the conveyer bed.

Embodiment 2 is the system of embodiment 1, wherein the peak wavelength can be between 200 nm and 280 nm.

Embodiment 3 is the system of any one of embodiments 1-2, wherein the brushing device antimicrobial compound can be selected from a group consistent of a nanoparticle, an antibiotic compound, an oxide, and a catalyst for the formation of a reactive oxygen species.

Embodiment 4 is the system of any one of embodiments 1-3, wherein the brushing device antimicrobial compound can be reactive with light of a peak wavelength between 200 nm and 750 nm.

Embodiment 5 is the system of any one of embodiments 1-4, wherein the brushing device antimicrobial compound can be reactive with light of a peak wavelength between 200 nm and 280 nm.

Embodiment 6 is the system of any one of embodiments 1-5, wherein the one or more brushes can include bristles.

Embodiment 7 is the system of any one of embodiments 1-6, wherein the bristles can be coated with the antimicrobial compound.

Embodiment 8 is the system of any one of embodiments 1-7, wherein the bristles can be infused with the antimicrobial compound.

Embodiment 9 is the system of any one of embodiments 1-8, wherein the coating device can include a heating element and a spraying device, the coating device configured to heat the coating mixture to a first temperature before application of the coating mixture to the plurality of products on the conveyor bed.

Embodiment 10 is the system of any one of embodiments 1-9, wherein the coating device can be configured to heat the coating mixture to the first temperature and deliver the coating mixture onto the plurality of the products at a second temperature, the first temperature greater than the second temperature.

Embodiment 11 is the system of any one of embodiments 1-10, wherein the coating mixture can include a second antimicrobial compound.

Embodiment 12 is the system of any one of embodiments 1-11, wherein the second antimicrobial compound can be a metal oxide nanoparticle.

Embodiment 13 is the system of any one of embodiments 1-12, wherein the second antimicrobial compound can be activated by exposure to ultraviolet radiation.

Embodiment 14 is the system of any one of embodiments 1-13, wherein the second antimicrobial compound can include zinc oxide.

Embodiment 15 is the system of any one of embodiments 1-14, wherein the coating mixture can include a monoglyceride and fatty acid salt.

Embodiment 16 is the system of any one of embodiments 1-15, wherein the coating mixture can include between 50% and 99% monoglyceride.

Embodiment 17 is the system of any one of embodiments 1-16, wherein the coating mixture can include between 1% and 50% fatty acid salt.

Embodiment 18 is the system of any one of embodiments 1-17, wherein the fatty acid salt can include a C16 fatty acid salt and a C18 fatty acid salt.

Embodiment 19 is the system of any one of embodiments 1-18, wherein the products can be perishable products.

Embodiment 20 is the system of any one of embodiments 1-19, wherein the products can be non-edible products.

Embodiment 21 is a product coating system, including a plurality of sprayers configured to dispense a coating mixture; and a heating element configured to heat the coating mixture to a first temperature.

Embodiment 22 is the system of embodiment 21, wherein the heating element can be configured to heat the coating mixture to the first temperature and deliver the coating mixture onto a plurality of products at a second temperature, the first temperature greater than equal to the second temperature.

Embodiment 23 is the system of any one of embodiments 21-22, comprising a vessel in fluid communication with the plurality of sprayers and configured to hold the coating mixture.

Embodiment 24 is the system of any one of embodiments 21-23, wherein the heating element can be configured to heat coating mixture within the vessel.

Embodiment 25 is the system of any one of embodiments 21-24, wherein the heating element can be configured to heat coating mixture downstream of the vessel.

Embodiment 26 is the system of any one of embodiments 21-25, wherein the coating mixture can include an antimicrobial compound.

Embodiment 27 is the system of any one of embodiments 21-26, wherein the coating mixture can include a monoglyceride and fatty acid salt.

Embodiment 28 is the system of any one of embodiments 21-27, wherein the coating mixture can include between 50% and 99% monoglyceride.

Embodiment 29 is the system of any one of embodiments 21-28, wherein the coating mixture can include between 1% and 50% fatty acid salt.

Embodiment 30 is a treatment system for a product, including means for reducing a microbial load on a surface of a product.

Embodiment 31 is a method for treating a product, including removing a plurality of particulates from a surface of an product; exposing the surface of the product to a light of a first wavelength; heating a coating mixture to a first temperature; coating the product with the heated coating mixture.

Embodiment 32 is the method of embodiment 31, wherein removing the plurality of particulates can include brushing the surface of the product with an antimicrobial brush.

Embodiment 33 is the method of any one of embodiments 31-32, wherein the antimicrobial brush can include an antimicrobial compound selected from a group consistent of a nanoparticle, an antibiotic compound, and an oxide.

Embodiment 34 is the method of any one of embodiments 31-33 comprising, after heating the coating mixture to the first temperature, cooling the cooling the coating mixture to a second temperature before coating the product with the heated coating mixture.

Embodiment 35 is the method of any one of embodiments 31-34, wherein the first wavelength can be between 200 nm and 280 nm.

Embodiment 36 is the method of any one of embodiments 31-35, wherein the coating mixture can include an antimicrobial compound.

Embodiment 37 is the method of any one of embodiments 31-36, wherein the antimicrobial compound can be activated by exposure to ultraviolet radiation.

Embodiment 38 is the method of any one of embodiments 31-37, wherein the coating mixture can include a monoglyceride and fatty acid salt.

Embodiment 39 is the method any one of embodiments 31-38, wherein the fatty acid salt can include a C16 fatty acid salt and a C18 fatty acid salt.

Embodiment 40 is the method of any one of embodiments 31-39, wherein the products can be perishable products.

Embodiment 41 is the method of any one of embodiments 31-40, wherein the products can be non-edible products.

Embodiment 42 is a treatment system, including a coating device that delivers a coating mixture onto a plurality of products; and a UV sterilization system in fluidic communication with the coating device, the UV sterilization system including a UV light source that emits light in a wavelength range of 100 nm to 400 nm.

Embodiment 43 is the treatment system of embodiment 42, wherein the UV sterilization system can include a reaction chamber having a fluid inlet and a fluid outlet.

Embodiment 44 is the treatment system of any one of embodiments 42-43, wherein the UV light source can be at least partially encased within the reaction chamber.

Embodiment 45 is the treatment system of any one of embodiments 42-44, wherein the coating device can include a sprayer.

Embodiment 46 is the treatment system of any one of embodiments 42-45, wherein the coating device can include a brush bed.

Embodiment 47 is the treatment system of any one of embodiments 42-46 which can include a coating mixture source in fluidic communication with the coating device.

Embodiment 48 is the treatment system of any one of embodiments 42-47, wherein the UV sterilization system can be located between the coating mixture source and the coating device to treat the coating mixture before it can be delivered by the coating device.

Embodiment 49 is the treatment system of any one of embodiments 42-48, wherein the coating device can include a submersion bath.

Embodiment 50 is the treatment system of any one of embodiments 42-49, wherein the coating device can include a fluid recirculation circuit that recirculates coating mixture from the submersion bath.

Embodiment 51 is the treatment system of any one of embodiments 42-50, wherein the UV sterilization system can be located along the fluid recirculation circuit.

Embodiment 52 is the treatment system of any one of embodiments 42-51, wherein the coating mixture can include a monoglyceride and fatty acid salt.

Embodiment 53 is the treatment system of any one of embodiments 42-52, wherein the fatty acid salt can include a C16 fatty acid salt and a C18 fatty acid salt.

Embodiment 54 is the treatment system of any one of embodiments 42-53, wherein the products can be perishable products.

Embodiment 55 is the treatment system of any one of embodiments 42-54, wherein the products can be edible products.

Embodiment 56 is the treatment system of any one of embodiments 42-55, wherein ambient light can activates the antimicrobial properties of the coating.

Embodiment 57 is a method for treating a product, including removing a plurality of particulates from a surface of a product; exposing the surface of the product to a light of a first wavelength; heating a coating mixture to a first temperature; and coating the product with the heated coating mixture using antimicrobial brushes.

Embodiment 58 is a method for treating a product, including removing a plurality of particulates from a surface of a product; heating a coating mixture to a first temperature; coating the product with the heated coating mixture using antimicrobial brushes; and exposing the surface of the product to a light of a first wavelength.

The details of one or more implementations are set forth in the accompanying drawings and the description below. Other features and advantages will be apparent from the description and drawings, and from the claims.

DETAILED DESCRIPTION OF ILLUSTRATIVE EMBODIMENTS

Figure 1:
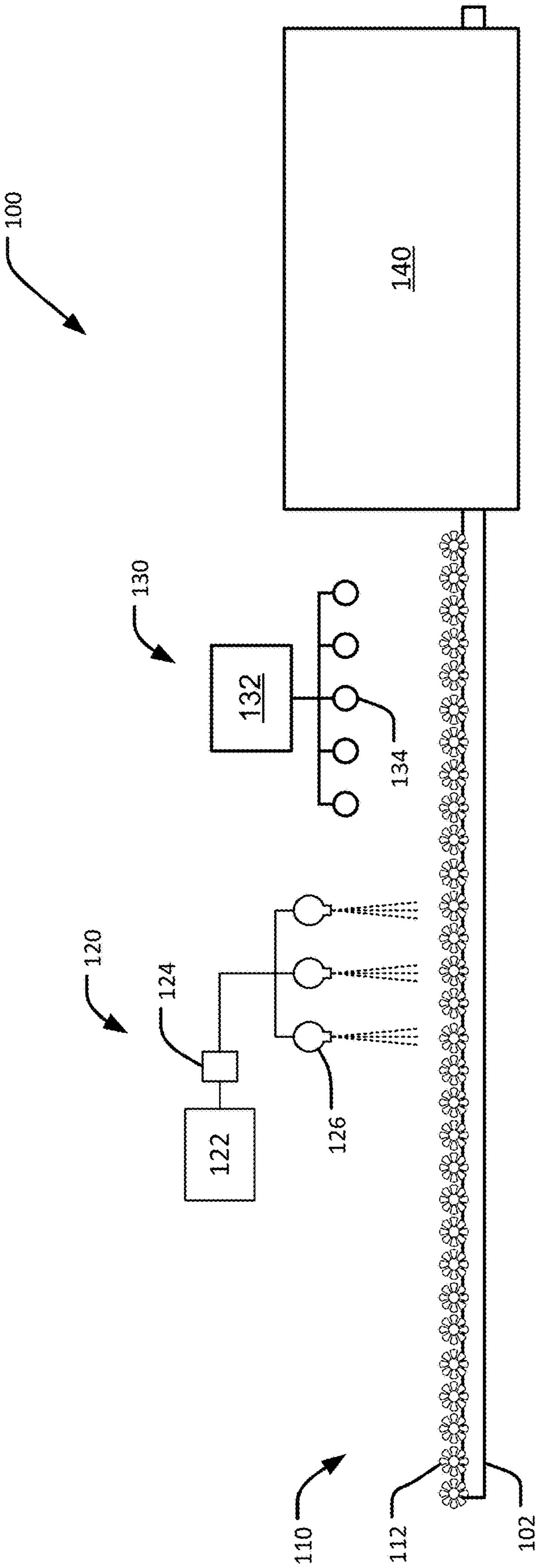
FIG. 1 schematically illustrates an example treatment system including apparatuses for brushing, coating, and applying UV radiation to a product.

Referring to FIG. 1, an example treatment system 100 is shown. The treatment system 100 is configured to treat the surface of products, such as food products, harvested produce or other agricultural products, seeds, non-food products, packaging, etc., thereby reducing microbial load and forming a coating on the products. The treatment system 100 includes apparatuses to reduce the microbial load of food products, such as through surface brushing or preventing the cross contamination of products, UV surface treatment, and/or application of a heated coating solution. The treatment system 100 can further include a drying tunnel 140 to facilitate drying of a coating solution (e.g., a high water-content coating).

Beginning from the left of FIG. 1, the treatment system 100 can include a conveyer 102 configured to move product through the treatment apparatuses of system 100. In general, the treatment system 100 can further be used with, or include, an infeed system, a bed, and/or a packing station. The conveyor 102 transports products between the respective treatment apparatuses of the system 100. For example, the conveyor 102 includes a conveyor bed configured to transport products from one end of the treatment system 100 to the opposing end, such as via a rolling translating conveyer. In an example embodiment, the conveyor 102 of FIG. 1 is a continuous conveyor bed that extends from a first end of the treatment system 100 to a second, opposite end. Alternatively or additionally, the conveyor 102 can be composed of multiple sequential conveyors arranged to coordinate the transport of product through the treatment system 100.

Treatment system 100 includes a brushing device 110 composed of one or more brushes 112 arrayed along the longitudinal axis of the conveyor 102. The brushes 112 agitate the exposed surfaces of the products and remove particulates. The brushes 112 can be oriented such that distal ends of brush 112 contact the exposed product surfaces. The brushing device 110 can operate the brushes 112 to cause product motion in parallel with the directionality of the conveyor 102, or cause product tumbling motion to promote uniform and consistent exposure of product surfaces to bristle agitation. In an example embodiment, brush 112 includes bristles having antimicrobial characteristics that promote removal and reduction microbial load on the bristles before transport to downstream components of the treatment system 100. Additional information on the brushing device 110 is explained with reference to FIGS. 2A and 2B below.

In some embodiments, treatment system 110 includes a coating device 120 that can apply a coating material to products. For example, the coating device 120 includes a vessel 122 that defines a volume to hold and/or prepare liquid material and additives, a heating element 124, and one or more sprayers 126. The vessel 122 stores a coating mixture for application to product surfaces traversing the conveyor 102 beneath. In some implementations, the coating device 120 operates one of the conveyors composing the multiple sequential conveyors of the treatment system 100.

The vessel 122 dispenses coating mixture to the heating element 124 (e.g., an in-line heating element) which raises the temperature of the material to a predetermined temperature. Increasing the temperature of the coating mixture to a predetermined value, or maintaining the temperature at a predetermined value, can deactivate microbial load that may be present before/during application. The heated coating material is then directed to one or more sprayers 126 which disperse the liquid material onto exposed product surfaces.

In an example embodiment, the elevated temperature of the coating material can also promote deactivation of microbial load present on the exposed product surfaces. In various example embodiments, the coating material may be heated to a temperature between 50° C. and 100° C., 60° C. and 90° C., or about 80° C. In some examples, the temperature is between 55° C. and 65° C. just before exiting from a delivery nozzle (e.g., of a sprayer). Such temperature ranges can effectively reduce microbial loading, without adversely impacting the product being coated.

In some implementations, the coating mixture can, as an alternative or addition to heating the coating mixture, contain antimicrobial compounds or elements that reduce microbial load on product surfaces.

Treatment system 100 includes a surface treatment device 130 with control electronics 132 and one or more lamps 134 that expose product surfaces to UV light. UV light between 200 nm and 280 nm, e.g., UVC, promotes deactivation of microbes through destruction of the chemical bonds in microbial DNA. This short-wave ultraviolet light disrupts DNA and RNA base pairing (e.g. crosslinking between DNA pairs, photochemical modification and other oxidative damage) and leads to the inactivation of bacteria, viruses, and protozoa. In some embodiments, short wavelength UVC provides an irradiative deactivation of the microbial load without negatively altering the product. For example, the short wavelength of UVC (e.g., <280 nm), interacts with and disrupts the chemical bonds of microbial nucleic acid present on product surfaces while constraining photon penetration of the product, such as photon penetration of less than 200 μm, less than 100 μm, or less.

In addition, exposure to UV light may trigger host defense upregulation, leading to increased resistance of the produce to pathogens and spoilage organisms.

Treatment system 100 optionally includes drying tunnel 140. The drying tunnel 140 can include various components to facilitate drying (e.g., dehydrating) the coating mixture on the products, for example heated air blowers, drying brushes, and drying tunnels with roller conveyors. The drying tunnels may include air recirculation and/or humidity control systems that utilize ventilation ducts and modulating exhaust. High pressure blowers may be provided to supply air to a perforated plate, which can promote high air velocity across the product path.

In various example embodiments, the brushing device 110, coating device 120, and/or surface treatment device 130, can be arranged before, within, and/or after drying tunnel 140. For example, treatment apparatus may include brushing device 110, coating device 120, and surface treatment device 130 in sequence to treat product before the product enters drying tunnel 140. Alternatively or additionally, coating device and/or surface treatment device may be included at entry and/or exit locations of drying tunnel 140.

In further example embodiments, brushing device 110, coating device 120, and/or surface treatment device 130, can be arranged as described herein or in alternative sequences to provide increased removal of microbial load. For example, in embodiments in which the coating mixture includes antimicrobial components activated by UV light, the surface treatment device 130 can be arranged following the coating device. Alternatively, the brushing device 110 preceding surface treatment device 130 removes macroscopic (e.g., >100 μm) particulates that can harbor microscopic microbes. The removal of macroscopic particulates improves the deactivation efficiency of UV radiation by increasing product surface exposure.

In some embodiments, treatment system 100 includes one or more microbial load reduction device such as brushing device 110, coating device 120, and/or surface treatment device 130. The devices 110, 120, and 130 can be used independently, in sequence, in parallel, or in any combination in addition to the sequences described herein.

Figure 2A:
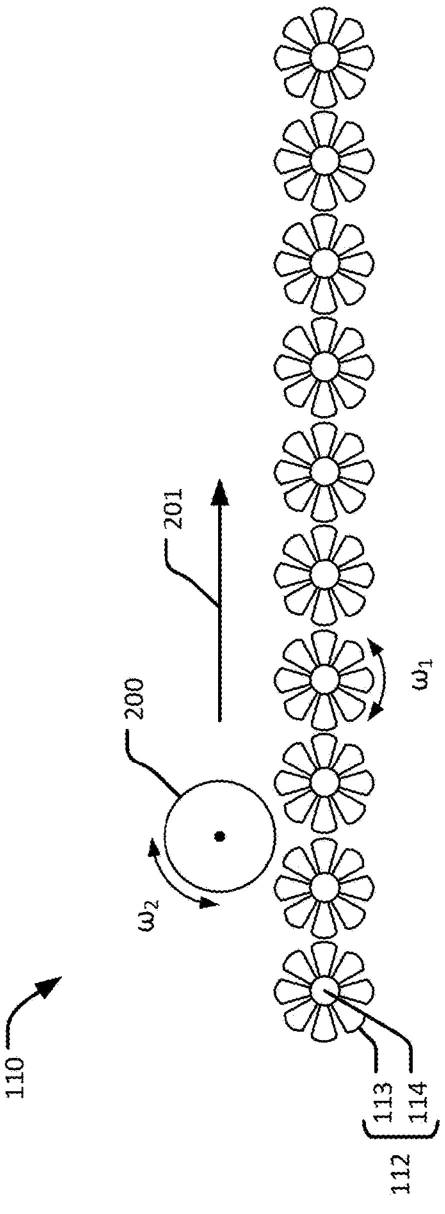
FIGS. 2A-2B schematically illustrate an example brush roller apparatus.
Figure 2B:
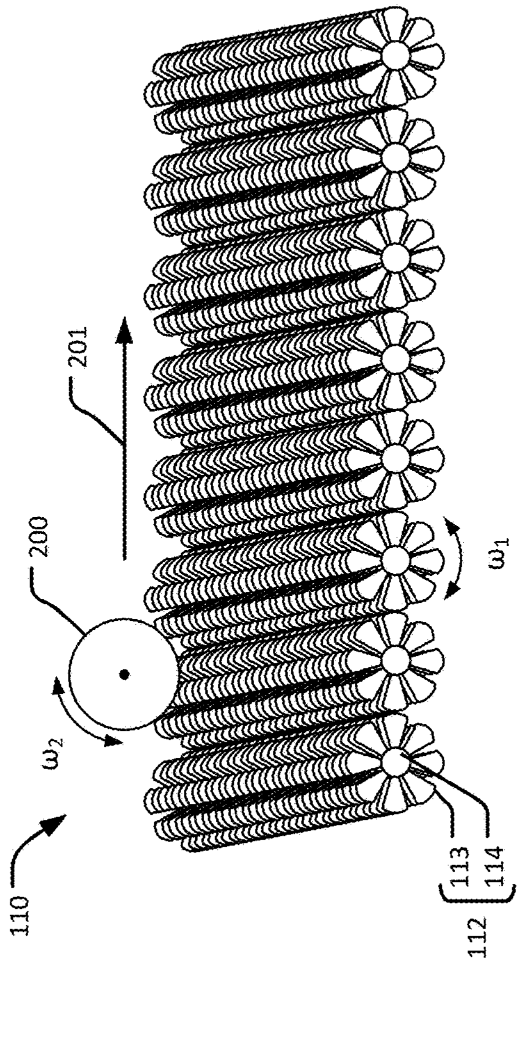

Referring now to FIGS. 2A and 2B, side and perspective views of brushing device 110 is shown. Brushing device 110 includes one or more brushes 112. In some embodiments, the brushes 112 include elongated bristles 113 attached to a core 114, e.g., a shaft, head, or spindle, which extend in parallel into the plane of the page. FIGS. 2A and 2B depict an example arrangement in which the parallel longitudinal axes of the brushes 112 are co-planar and transverse to the direction 201 of product 200 travel. Alternatively or additionally, brushes 112 can include circular, coiled, or strip shapes, and/or brushes 112 can include foam, rubber, fabric, polymer portions configured to contact and/or remove matter from product surfaces.

The number, type, size, or composition of the brushes 112 can be selected based upon the product 200 in the treatment system 100. For example, transverse arrangements can be used to promote effective agitation/translation of spherical products (e.g., apple, orange), and/or longitudinal arrangements can be used to promote effective agitation/translation of cylindrical products (e.g., carrot).

Brushing device 110 operates the brushes 112 to create relative motion between the distal ends of the brushes 112 (e.g., distal ends of the bristles 114) and the surface of the product 200. In various example embodiments, brushes 112 can agitate product 200 through rotational, translational, vibratory, or other motion. Optionally, the brushing device 110 can operate the brushes 112 to induce product 200 travel along the treatment system 100. For example, by operating brushes 112 at a common rotational speed, w, such as a belt- or chain-driven system connecting all brushes 112, distal bristle ends contact the product 200 and induce motion along the travel direction 201. In some implementations, each brush 112 operates at non-equal rotational speeds to induce rotational motion in the product 200 at a given rotational speed, $\omega_2$ (e.g., tumbling). Added product 200 rotational motion can homogenize surface contact exposure to the bristles 114, removing particulates uniformly across the product 200 surface. The brushing device can operate independently from the conveyor 102 drive system, or dependently.

The bristles 114 can be composed of natural (e.g., horsehair), or synthetic (e.g., PTFE, polyethylene, polystyrene, polyether sulfone, or nylon) material, or a combination of materials. Bristle 114 density and stiffness are parameters that influence particulate removal from product 200 surfaces. In some embodiments, relatively high stiffness and/or density can enhance surface agitation for product 200 having a relatively hard outer surface, and or relatively low stiffness and/or density can remove particulate without damaging product having relatively soft surface.

In an example embodiment, brushes 112 include one or more antimicrobial agents to increase deactivation of microbial load following particulate removal and decrease cross contamination of subsequent product 200. The antimicrobial agents can include silver, copper, zinc oxide nanoparticles, or combinations thereof.

For example, antimicrobial agents can be included in the construction of synthetic bristles 114. In further examples, the bristles 114 can be coated in antimicrobial agents, or antimicrobial agents chemically cross-linked to the surfaces of the bristles 114. In some implementations, the antimicrobial compound can be coated on the surface of the bristles 114 such that when product 200 contacts the bristles 114, antimicrobial compound is deposited onto the product 200 surface. In some embodiments, the bristles can be constructed of a polymer that is co-extruded or blended with an antimicrobial agent.

The bristles 114 can be treated to receive antimicrobial compounds into the bristle 114 structure. For example, bristles 114 including natural bristles, such as horsehair bristles 114, are primarily composed of keratin, a fibrous protein structure. Processing the bristles 114 with a disulfide bond-breaking treatment (e.g., sodium dithionite, dithiothreitol, etc.) disrupts disulphide bridges between thiol groups of neighboring cysteine molecules. The thiol groups are then available for reaction with thiol groups, or sulfur/nucleophile reactive groups, of selected antimicrobial compounds or elements which can be introduced to the bristles 114, such as via bulk treatment in liquid submersion or spray-coating.

Microbe-laden particulate removal via brushing device 110 increases the efficacy of downstream microbial load reduction devices such as coating device 130. Reducing the amount of macroscopic particulates present on product surfaces allows increased uniformity in product coating thickness and adhesion by removing loosely attached elements, such as the particulates. Particulate removal from product surfaces reduces cross-contamination of products when product coating is applied.

Figure 3A:
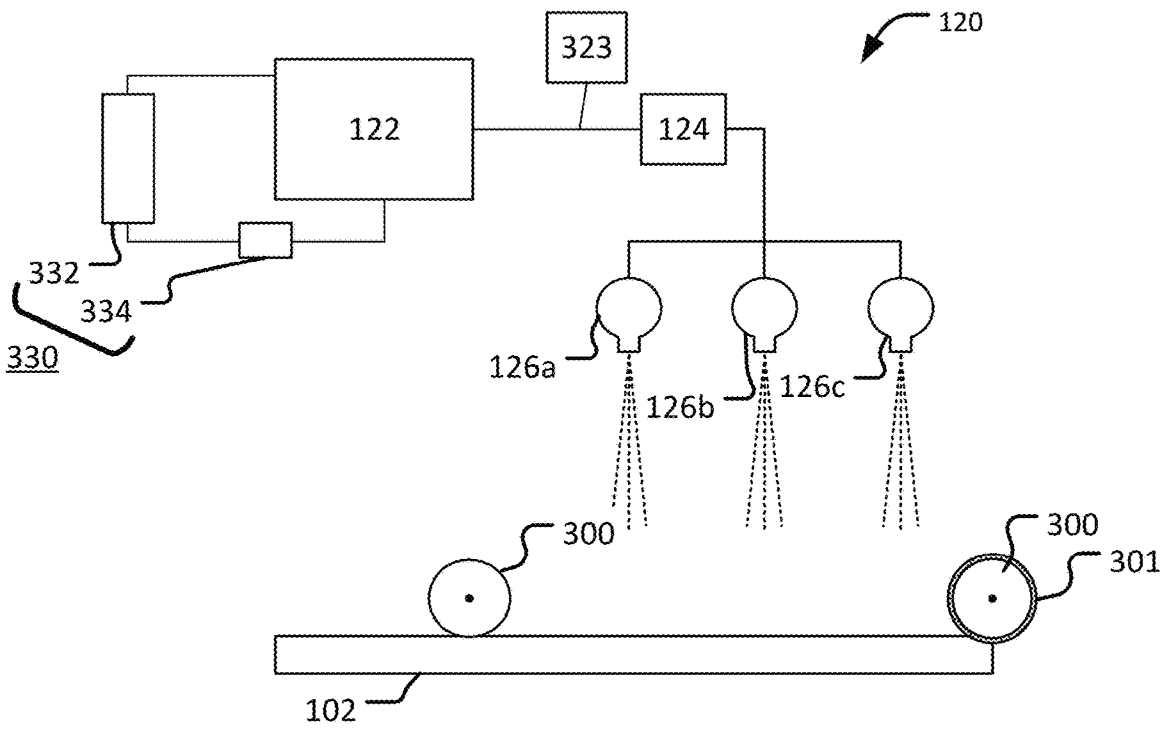
FIG. 3A schematically illustrates an example heated surface coating treatment system.

FIG. 3A depicts the coating device 130 of FIG. 1 in greater detail. The coating device 130 facilitates application and formation of protective coatings (e.g., edible coatings) on products 200. As described above, the coating device includes a vessel 122 for holding liquid material, a heating element 124, and one or more sprayers 126 (e.g., sprayers 126*a*-126*c*). In some implementations, the coating device 130 can include one or more tanks 323 to hold additives for mixing into the coating mixture before or after heating.

In some example implementations, the vessel 122 is in fluidic communication with a sterilization system 330. A sterilization system 330 can provide a reduction of the coating mixture microbial load before or during application to a product 300 or conveyor 102.

The sterilization system 330 includes a reactor vessel 332 and a fluid pump 334 along a fluid circuit with the vessel 122. The fluid pump 334 operates to draw coating mixture from the vessel at a first fluid connection. The fluid pump 334 can operate continuously and/or intermittently to achieve a flow rate or exposure time based upon at least the sterilization thresholds of the coating mixture and the reactor vessel 332. Examples of fluid pump 334 can include diaphragm, plunger, positive displacement, or velocity pumps and the type of fluid pump 334 can be selected based upon the coating mixture to be circulated, for example. In some embodiments, a diaphragm pump can promote sterility and/or equipment cleanliness. The fluid pump 334 flow rate can depend on the instant volume of coating mixture within the reactor vessel, the emitted light path length, and the absorption coefficient (a) of the liquid at the emitted wavelength, λ, but in some examples can be in the range of 0.1 gal/min to 10 gal/min.

Figure 3B:
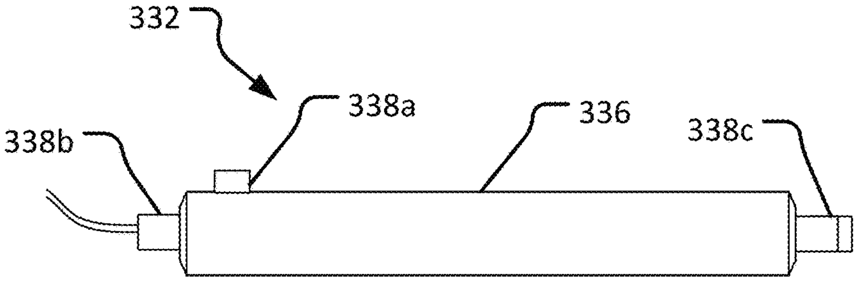
FIGS. 3B-3D schematically illustrate an example reactor vessel of a sterilization system.
Figure 3C:
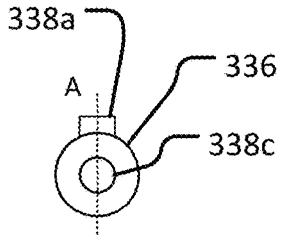

Coating mixture drawn from the vessel 122 is directed to the reactor 332 (e.g. by the fluid pump 334). The reactor 332 includes a reaction chamber 338 encasing a light source, as shown in FIG. 3B. The reaction chamber 336 is cylindrical having a length and a diameter and includes three ports 338*a*, 338*b*, and 338*c*. Ports 338*a* and 338*c* are liquid ports through which coating mixture travels along the fluid circuit. Liquid entering one port (338*a* or 338*c*)(e.g., fluid inlet) flows through the reaction chamber 336 in the volume separating the inner surface of the reaction chamber 336 and the outer surface of the light source and exits the opposing port (338*c* or 338*a*, respectively)(e.g., fluid outlet). Port 338*b* provides a liquid-sealed entrance and connection for the enclosed light source to be installed within the reaction chamber. A view along the longitudinal axis of the reactor chamber is shown in FIG. 3C, including a cross-sectional view line (A) depicting the view of FIG. 3D. To one skilled in the art, it should be obvious that any combinations of or orientations of ports is possible, as well as a configuration in which the fluid flows past multiple bulbs, or where the solution flows through a single or multiple transparent tubes surrounded by bulbs.

Figure 3D:
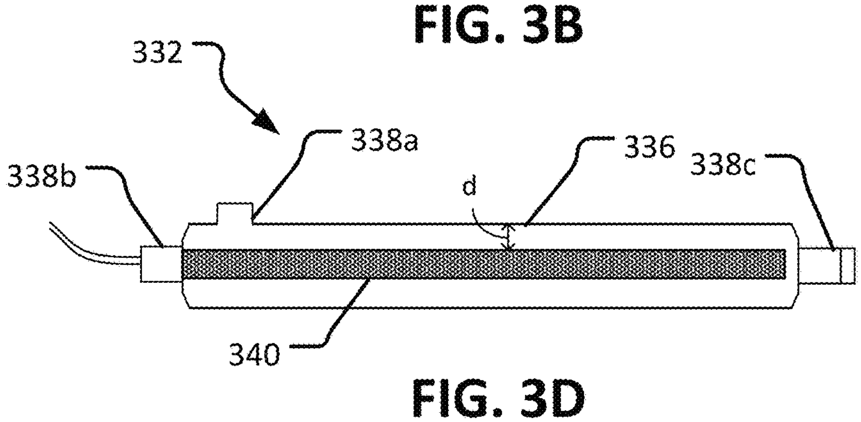

Referring to FIG. 3D, an interior cross-sectional view of the reactor 332 along line A of FIG. 3C is shown. The interior of the reactor 332 shows the distance, d, between the outer surface of the light source 340 and the inner surface of the reaction chamber 336. The reactor 332 receives the coating mixture through port 338*a* into the inner volume where it is exposed to the light source 340 emitting light of a wavelength, λ. In various implementations, the light source 340 is a UV light source 340 emitting light in the wavelength range of 100 nm to 400 nm, such as in the range of 230 nm and 260 nm. Light of sufficient intensity within these wavelengths can deactivate microbial load present in liquid products and on product surfaces. A sterilization system 330 including a UV light source 340 can be considered a UV sterilization system 330. To one skilled in the art it should be obvious that the wavelength should be chosen to eliminate microbial contamination without damaging the components of the solution (e.g. if the solution is based on water and contains organic components, wavelengths of below 200 nm can trigger photochemical dissociation of water to result in the destruction of the organic molecules).

Within the reaction chamber 336, the coating mixture flows between ports (e.g., 338*a* or 338*c*) in the volume separating the inner surface of the reaction chamber 336 and the outer surface of the light source 340. The volume is defined by the length of the inner surface of the reaction chamber 336 and the radial distance, d, separating the reactor chamber 336 inner surface and the light source 340 outer surface.

The emitted light from the light source 340 penetrates the coating mixture to a depth, d, and delivers a dose (D), which describes an amount of energy applied for a time within a volume. D is a function of the light intensity entering the liquid, radial distance between surfaces (d), volume, residence time, and absorption coefficient (a) of the liquid at the emitted wavelength, λ. For example, in some embodiments, the total dose to a liquid volume can be estimated as:

$$D\left(\text{mW}\cdot\frac{s}{\text{cm}^3}\right) \propto \frac{UV \text{ intensity}\left(\frac{\text{mW}}{\text{cm}^2}\right)\times \text{residence time }(s)\times (1-\exp^{-d})}{a_\lambda \times V}$$

The lamp intensity, radial distance between surfaces (d), reactor chamber length, and flow rates (e.g., residence times) can be controlled such that the estimated dose meets or exceeds a dose threshold for reducing microbial load in the coating mixture introduced to the reaction chamber 336. Coating mixture exiting the sterilization system 330 is returned via liquid connection to the vessel 122 with reduced microbial load. For example, an estimated dose threshold of 10 mWs/cm$^3$ or more can achieve a reduction in the microbial load of the coating mixture.

The light intensity of a given wavelength, λ, decreases exponentially with increasing penetration depth of the emitted light. Therefore, decreasing the radial distance between surfaces (e.g., penetration depth) (d), increases the average dose rate for a given volume of coating mixture flowing through the inner volume. For example, the reactor vessel 332 can include radial distances, d, in a range from 0.1 cm to 20 cm (e.g. 0.5 cm to 5 cm). Dose also increases with reactor vessel 332 length, for example, including lengths in a range from 0.1 m to 5 m. Reactor vessel 332 configurations including high aspect ratios (e.g., relatively low radial distances, d, and relatively high lengths) can increase the average total dose delivered to a volume of coating mixture and decrease the variability of total delivered dose per volume of coating mixture treated in the reactor vessel 332.

In various embodiments, various configurations of the reactor vessel 332 achieve similar dose rates, and/or average total doses. For example, helical light sources 340 inside a cylindrical reaction chamber 336 can achieve higher emitted intensities and surface areas per reaction chamber 336 inner volumes. Alternatively or additionally, the reactor vessel 332 can include non-cylindrical reaction chambers 336 such as helical, or spheroidal, and/or non-linear configurations including one or more corner. In various alternative embodiments, the sterilization system 330 can include more than one reactor vessel 332, and/or more than one light source 340, to achieve similar dose rates, and/or average total doses.

In some embodiments, the sterilization system 330 and/or light source 340 can be integrated into one or more components of the coating device 120 reduce microbial load (e.g., in the coating mixture). The light source 340 can be arranged within, arranged in-line with, or integrated with one or more components of the coating device 120. For example, the light source 340 can be arranged within the interior volume of the vessel 122, within the interior volume of the tank 323, in-line between the vessel 122 and the tank 323, in-line between the vessel 122 and the heating element 124, or in-line between the heating element 124 and the sprayers 126. In such embodiments, the coating system 120 may not include the fluid pump 334 of the sterilization system 330.

In some embodiments, the treatment system 100 can include a material reclamation system which receives excess coating mixture shed from products 300. The material reclamation system can direct excess coating mixture to one or more components of the treatment system 100, such as components of the coating device 120, to be re-applied to subsequent products 300. In such embodiments, a sterilization system 330 in-line between the material reclamation system and destination components can reduce microbial load introduced during reclamation. This can include the reactor vessel 332 and fluid pump 334, and/or a light source 340 in-line between the material reclamation system and destination components.

The vessel 122 contains the coating mixture to be dispensed to product 300 surfaces. For example, while the product 300 moves (e.g. laterally in the view of FIG. 3A) along conveyor 102, the sprayers 126*a*-126*c* can spray or otherwise distribute droplets of a treatment agent (e.g., a solution, suspension, emulsion, etc.) over the surface of the product 300. The coating mixture can include a coating agent (e.g., a solute) in a solvent. Once the product is covered with the coating mixture, it passes beneath blower exhausts which facilitate controlled removal (e.g., via evaporation) of the solvent while the product 300 is on the conveyor system 102, allowing the coating agent to remain on the surface of the product 300 to form the protective coating 301. In some implementations, a single coating 301 is applied to the product 300. Alternatively or additionally, multiple coatings (e.g., of the same or different coating material) may be applied.

The protective coating 301 formed from the solute composition can be used to prevent food spoilage due to, for instance, moisture loss, oxidation, or infection by a foreign pathogen. The solvent in which the coating agent is dissolved or suspended can, for example, be water, an alcohol (e.g., ethanol, methanol, isopropanol, or combinations thereof), acetone, ethyl acetate, tetrahydrofuran, or combinations thereof. The coating agent can, for example, include monoacylglycerides, fatty acids, esters (e.g., fatty acid esters), amides, amines, thiols, carboxylic acids, ethers, aliphatic waxes, alcohols, fatty acid salts, organic salts, inorganic salts, or combinations thereof. In some implementations, the coating agent includes monomers, oligomers, or combinations thereof, including esters or salts formed thereof. In some implementations, the solutions/suspensions/colloids include a wetting agent or surfactant which cause the solution/suspension/colloid to better spread over the entire surface of the substrate during application, thereby improving surface coverage as well as overall performance of the resulting coating. In some implementations, the solutions/suspensions/colloids include an emulsifier which improves the solubility of the coating agent in the solvent and/or allows the coating agent to be suspended or dispersed in the solvent. The wetting agent and/or emulsifier can each be a component of the coating agent, or can be separately added to the solution/suspension/colloid.

In various embodiments, the coating agent can include a monoglyceride and a fatty acid salt. In some embodiments, the coating material further includes antimicrobial compounds or elements to deactivate microbes present on the surface of the product 300 during and following protective coating 301 formation further reducing the microbial load. Antimicrobial compounds or elements added to the coating mixture can be essential oils derived from plants (e.g., basil, thyme, oregano, cinnamon, clove, and rosemary), enzymes obtained from animal sources (e.g., lysozyme, lactoferrin), bacteriocins from microbial sources (e.g., nisin, natamycin), organic acids (e.g., sorbic, propionic, citric acid) and naturally occurring polymers (e.g., chitosan). The antimicrobial activity can depend on the chemical structure of the antimicrobial compound, including the presence of hydrophilic functional groups, such as hydroxyl groups of phenolic components.

In some implementations, the antimicrobial compound is a nanoparticle, such as an elemental (e.g., pure elemental silver or gold nanoparticles) or a molecular nanoparticle. Examples of molecular nanoparticle include a metal oxide nanoparticle (e.g., silver oxide ($Ag_2O$), copper oxide (CuO), iron oxide ($Fe_2O_3$), magnesium oxide (MgO), titanium oxide ($Ti_2O$), and zinc oxide (ZnO)). For example, ZnO is a wide-band gap semiconductor which can generate reactive oxygen species on its surface which diffuse into nearby material and disrupt microbial membranes.

In some implementations, coating mixture is prepared in one or more mixing tanks before traveling to the heating element 124. Water and/or any other solvents or solutes can be supplied to the mixing tanks from outside the industrial equipment. The liquid in the tanks can be prepared by heating and/or mixing coating material components, adding a coating agent or other additive or solute, and pumping the undispersed mix through a controlled high shear device in a recirculation loop until the additive is well dispersed.

The coating mixture dispensed from the vessel 122 is directed to a heating element 124 before deposition by the sprayers 126*a*-126*c*. The heating element 124 can be a heat exchanger, in-line immersion heater, circulation heater, or any other suitable heating element 124 that raises the temperature of the coating mixture to a temperature value. For example, a circulation heater flows coating mixture over a heated element in the line of flow. The heating element can include temperatures sensors, such as resistance temperature detectors (RTDs) or thermocouples, to monitor process temperatures, such as input and output temperatures. The heating element 124 can heat the coating mixture to a temperature minimum value, or recirculate the liquid for a residence time within the heating element 124 to target a specified reduction in microbial load. Alternatively or additionally, the heating element 124 may be located to heat coating material within vessel 122 to a predetermined temperature for application by the sprayers 126.

In various example embodiments, the coating material may be heated to a temperature between 50° C. and 100° C., 60° C. and 90° C., or about 80° C. In some examples, the temperature is between 55° C. and 65° C. just before exiting from the sprayers 126.

In some implementations, the heating element 124 can increase the temperature of the coating mixture to a specified value that is higher than a temperature of the coating mixture when applied to the product. For example, the heating element 124 is controlled to heat the coating mixture to a first predetermined temperature to facilitate sterilization of the coating mixture, and the temperature of the coating mixture is then reduced to a second predetermined temperature lower than the first predetermined temperature (e.g., when dispensed from the sprayers 126) that can be applied to the product 300 without damaging a surface of the product. For example, the coating mixture may be heated to a first predetermined temperature between 75° C. and 100° C., 80° C. and 95° C., or about 90° C., and may be applied at a second predetermined temperature between 50° C. and 90° C., 50° C. and 85° C., or about 60° C. In some embodiments, heating to the first predetermined temperature higher than the temperature when applied to the product can facilitate sterilization of bacteria or pathogens introduced during mixing, packaging, storage, or water treatments systems. In some implementations, the sprayers 126 are set a distance apart from the product 300 to allow evaporative or conductive cooling of the droplets to reduce the average temperature of the dispensed coating material.

Application of coating mixture at an elevated temperature can improve the coating process and enhance performance of the dried coating on the product. In some embodiments, application of a heated coating solution can affect the vesicle wall structure to promote an improved barrier layer of the dried coating. In some embodiments, a drying time can be reduced. For example, application of a water-based coating mixture at an elevated temperature can promote evaporation of water content, reducing the time to form a dried coating on the product surface.

In an example embodiment, the coating mixture is delivered to the sprayers and sprayed towards underlying rollers and/or products 300 on the bed beneath the sprayers. Lines connecting the vessel 122, heating element 124, and sprayers 126 provide a controlled pressure/flowrate of liquid so that the amount and distribution of liquid sprayed over the equipment and products to be treated can be precisely controlled.

The one or more sprayers, for example 126*a*-126*c*, spray droplets of coating mixture onto exposed product 300 surfaces as product 300 passes beneath the sprayers 126*a*-126*c*. In some implementations, the liquid droplets can include a sanitizing agent such as ethanol or peracetic acid. Alternatively, the sprayers can indirectly treat or coat the products by saturating rollers over which the products moves. For example, in some implementations, the conveyor 102 under sprayers 126*a* can be a first type of brush roller configured to absorb liquid sprayed thereon by sprayer 126*a* and to subsequently brush it onto products 30 that come in contact with the brush roller. The rollers under the sprayers 126*b* can be the same as those under sprayer 126*a*, and/or can include a second type of brush roller which can, for example, be configured to promote multi-axial rotation of the product 300 underneath the sprayers 126*b*. The conveyor 102 rollers can move independently from the belt or chain drive system that moves the conveyor 102. The sprayers 126*a*-126*c* and conveyor 102 can be configured to control the residence time that products 300 are beneath the sprayers 126*a*-126*c* being coated.

Figure 4:
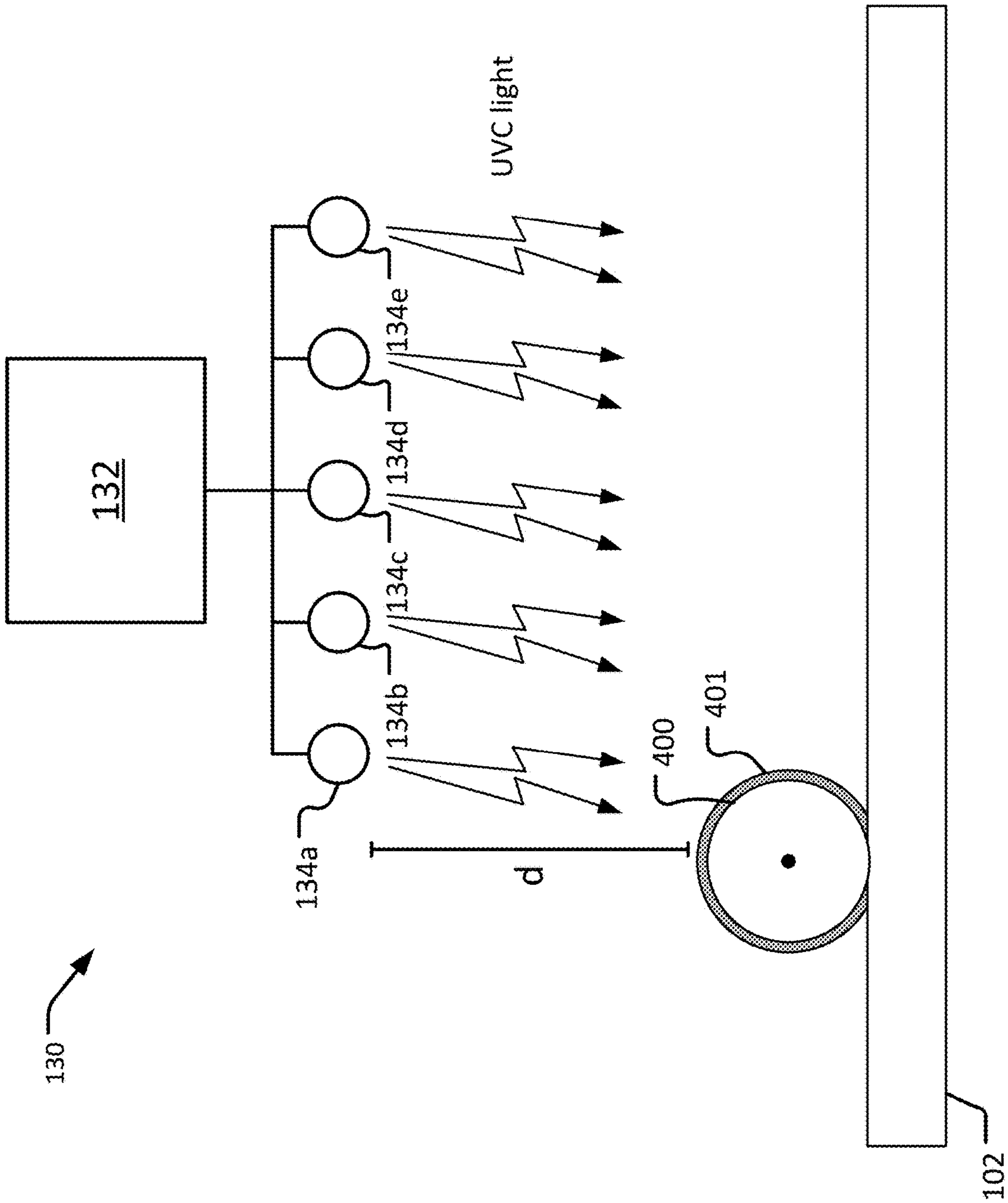
FIG. 4 schematically illustrates an example ultraviolet surface treatment system.

Treatment system 100 includes a surface treatment device 130 to sanitize product 300 surfaces and/or activate one or more antimicrobial compounds or elements within the protective coating 301. FIG. 4 depicts the surface treatment device 130 including control electronics 132 and lamps 134*a*-134*e* with product 400 including protective coating 401 beneath.

The control electronics 132 of the surface treatment device generate electronic control signals for connected UV lamps 134, including power converters, processors, memory, and/or ballast. In some implementations, the control electronics 132 can be configured to control the conveyor 402 rollers to control product 400 residence time beneath the lamps 134.

One or more UV lamps 134 that emit radiation in the ultraviolet spectrum, such as UV lamps 134*a*-134*e*, are electrically connected to the control electronics 132. UV lamps 134*a*-134*e* can include low-pressure mercury lamps, medium-pressure mercury lamps, high-pressure mercury lamps, excimer lamps, or light-emitting diodes (LEDs). Lamps 134 producing light in the wavelength range between 200 nm and 280 nm reduce microbial load though lamps 134 emitting between 250 nm and 260 nm reduce microbial load most efficiently. These wavelengths operate effectively against a broad spectrum of microbes due to the disruption of DNA or RNA base pairing. In some implementations, the control electronics 132 can operate the UV lamps 134 concurrently, or in a sequence as coated product 400 is beneath one or more UV lamps 134.

The quantity of UV radiation to which product 400 surfaces are exposed can be measured as a surface dose, such as $\mu W \cdot s/cm^2$ or $\mu J/cm^2$, similar to the volume dose described above. In surface applications, UV effectiveness can be estimated by calculating the UV dose delivered to the microbial load on the product 400 surface. For a surface area, the dose to a surface can be estimated as $$D(\mu W \cdot s/cm^2) \propto \frac{UV \text{ intensity } \left(\frac{\mu W}{cm2}\right) \times \text{residence time (seconds)}}{d^2}$$

UV intensity at a surface can be measured based on energy intensity ($\mu W/cm^2$) at a distance (d) from the UV lamp 134 and is inversely proportional to the square of the distance ($\propto 1/d^2$) between product 400 and UV lamp 134, decreasing at larger and increasing at smaller distances. The estimated UV intensity may be adjusted based upon at least the distance between UV lamp 134 and product 400.

The exposure time can be estimated as the time the product 400 spends within a minimum distance of at least one UV lamp 134 such that the intensity reaches or exceeds the targeted minimum. Exposure times can vary depending on average lamp intensity and distance to UV lamps 134 and can be between 1 second to 5 minutes, 5 seconds to 2 minutes, 1 second to 1 minute, 10 seconds to 1 minute, or about 20 second. In some embodiments, smaller distances between UV lamps 134 and product 400 surfaces can increase UV dosage and/or reduce exposure times.

In some implementations, the control electronics 132 can hold in memory a minimum UV dose value for the product 400 and a distance value for the average distance between the UV lamps 134 and product 400 surfaces. Alternatively, the control electronics 132 can include an intensity value to use for the UV lamp 134 distance to the conveyor. The control electronics 132 can additionally control the exposure time to meet the minimum UV dose value based upon the stored distance value or intensity value by moderating product 400 travel speed by increasing or decreasing the rotational velocity of conveyor 102 rollers beneath the product 400.

In some implementations, antimicrobial additives in the protective coating 401 can undergo reaction via the UV light thereby enhancing deactivation of the microbial load. For example, ZnO can be included in the coating mixture applied to products. Reactive oxygen species generation by ZnO present in the protective coating 401 can be enhanced by excitation with ultraviolet light, further reducing microbial load present on product 400 surfaces. In some embodiments, the antimicrobial additives can be activated or otherwise enhanced by ultraviolet light during the application and/or drying process. For example, the antimicrobial activity can be enhanced while the coating is at liquid or less than completely dried on the product surface. Alternatively or additionally, antimicrobial additives can be activated or otherwise enhanced after the coating has dried on the product surface. In some embodiments, the antimicrobial additive may be further activated or otherwise enhanced by sources of ultraviolet light downstream of the treatment system 100, such as by natural sources of ultraviolet light. In some embodiments, the protective coating 401 can undergo reaction via non-UV light, such as visible light (e.g., 300 nm to 750 nm).

Referring again to FIG. 1, the treatment system 100 can further include a drying tunnel 140 including various components for circulating conditioned air to dry products that are transported by the conveyor 102. For example, the drying tunnel 140 can include an intake blower configured to draw air into the drying tunnel 140, and an exhaust blower configured to discharge air from the drying tunnel 140. The drying tunnel 140 can further include a heating element to adjust a temperature of air circulating in the drying tunnel 140. One or more hot air recirculation control dampers can control volume of recirculated air and/or facilitate control of one or more air temperature and humidity values. The treatment system 100 can include one or more airflow control panels that are disposed at different locations in the apparatus and configured to control airflow at such locations. The drying tunnel 140 can include one or more fan assemblies that are disposed at different locations in the apparatus and configured to drive air flow at desired directions.

Figure 5:
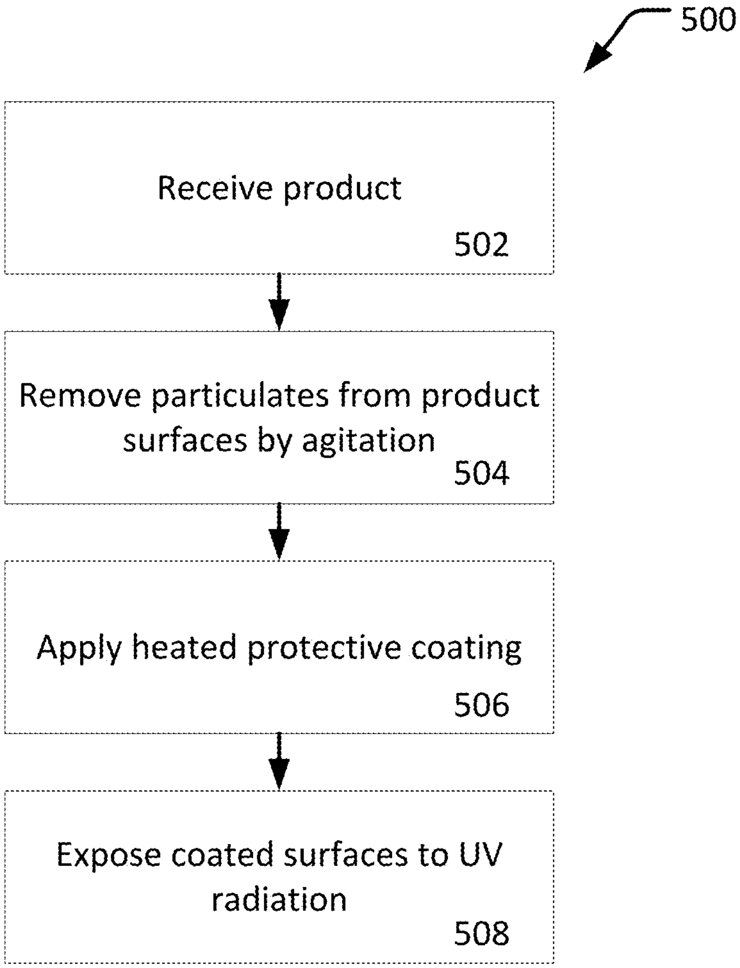
FIG. 5 is a flow diagram of an example method of treating products.

Referring now to FIG. 5, a flow diagram of an example method 500 of reducing the microbial load of product surfaces is shown. Method 500 includes receiving products 502, such as food products, harvested produce or other agricultural products, seeds, non-food products, packaging, etc. Receiving products can include products traversing a conveyor, products deposited from a hopper or sorting machine, or other product delivery methods.

Method 500 may include removing particulates from received product surfaces by agitation 504. For example, particulates can be removed from product surfaces using a brushing device that includes one or more brushes oriented such that distal ends of the brush contact the product's exposed surfaces. Relative motion between the distal ends of the brushes and product surfaces can promote removal of particulates from the product surfaces.

In example embodiment, operation 504 of removing particulates includes contacting product surfaces with brushes that include one or more antimicrobial agents, to increase deactivation of microbial load and decrease cross contamination of subsequent product. For example, the brushes can be coated in antimicrobial agents, or antimicrobial agents chemically cross-linked to surfaces of the brushes, or treated to receive antimicrobial compounds or elements into the brush structure.

Method 500 may further include application of a heated protective coating 506 to prevent food spoilage due to, for instance, moisture loss, oxidation, or infection by a foreign pathogen. Coating mixture including a coating agent (e.g., a solute) is prepared in one or more mixing tanks, in which additives or adjuncts can be added to the mixture before traveling to the heating element. The heating element heats the coating mixture to a temperature minimum value targeting a specified reduction in microbial load, improving the coating process, or enhancing performance of the dried coating on the product.

Protective coating is applied via sprayers distributing droplets of a treatment agent (e.g., a solution, suspension, emulsion, etc.) over the surface of the product. Alternatively or additionally, the sprayers can indirectly treat or coat the products by saturating rollers over which the products moves. In some embodiments, the protective coating is dried via evaporation or other means before traversing to the next station.

In some embodiments, method 500 may further include exposing coated surfaces to UV radiation 508. For example, operation 508 can include exposing surfaces to radiation emitted by one or more UV lamps. The UV lamps are operated to expose coated products to a measured dose of energy to reduce the microbial load present on coated product surfaces.

In some embodiments, the antimicrobial additives in the protective coating can undergo reaction via the UV light thereby enhancing deactivation of the microbial load. For example, reactive oxygen species generation by oxides present in the protective coating can be enhanced by excitation with ultraviolet light, further reducing microbial load present on product surfaces.

In various example embodiments of method 500, operations 502, 504, 506, and 508 may be performed in alternative sequences and/or combinations. For example, operation 506 may be performed after operation 508. Likewise, one or more operations may be performed independently or one or more operations may be omitted from method 500.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

EXAMPLES

The following examples describe effects of various antimicrobial brush bed treatments, as well as characterization of some of the various coating agents and exposure to antimicrobial light. These examples are only for illustrative purposes and are not meant to limit the scope of the present disclosure. In each of the examples below, all reagents and solvents were purchased and used without further purification unless specified.

Example 1: Method of Binding Metallic Nanoparticles to Horsehair Brush Samples

Materials and Preparation

Metallic nanoparticle suspensions (ZnO or Ag) or nanopowders (Cu) were purchased commercially (Sigma Aldrich). All other materials were purchased commercially and used without further purification.

30 g of horsehair obtained from a commercially-purchased brush was washed with deionized water three times. A buffered solution of sodium dithionite was prepared by adding 1 mL saturated sodium carbonate and 9 mL saturated sodium bicarbonate solution to a beaker, dilution to 1 L with deionized water, covering, and bubbling nitrogen through the solution for 15 minutes to deoxygenate the liquid.

80 g of sodium dithionite was added to the solution while stirring to produce a 1 M sodium dithionite solution. The solution was heated to 40° C. The horsehair was added to the solution while stirring and bubbling nitrogen, covered, and treated for 1.5 hours producing activated horsehair. After the activation, the activated horsehair was filtered from the solution and washed three times with deionized water, while minimizing exposure to air.

20 mg of copper (Cu) nanopowder and 10 mL of deionized water were added to a scintillation vial. The suspension was sonicated at 40 kHz sonication frequency at up to 80 Watts for one hour, and then shaken by hand, followed by sonicating for a second hour. For example, a Branson 1510R-MT sonicator can be used. Immediately prior to use, the solution was shaken vigorously by hand to resuspend any particulates.

Stock solutions of silver (Ag) and zinc oxide (ZnO) nanoparticles were purchased commercially and the Cu solution was prepared as described above. Nanoparticle stock solutions (NP) were added to 1 L of deoxygenated deionized water to a final concentration of either 0.5 mg NP/L or 20 mg NP/L. 5 g of activated horsehair was added to both solutions with stirring. The activated horsehair was treated at for 15 minutes, followed by isolating the treated horsehair by filtration and washing three times with 1 L deionized water. The treated horsehair was then dried under vacuum at 35° C.

Quantitation and Verification of Samples Using Inductively Coupled Plasma Atomic Emission Spectroscopy (ICP-OES)

~0.25 g of each treated horsehair sample and 10 mL of concentrated nitric acid was digested in a MARS 6 microwave digestion system to a temperature of 210° C. for 15 minutes. The digested samples were then diluted to 50 mL with distilled deionized water from a MilliQ water treatment system. An internal standard was prepared and used as following: a 1000 ppm stock solution of yttrium nanoparticles was purchased and diluted to 5 ppm using MilliQ water, which was introduced at a known rate to the sample induction system. Some samples required further dilution due to high metal content to prevent detector saturation.

Yttrium calibration standards were produced in a final concentration range from 0 ppm to 1 ppm and functioned as an internal QC standard. Samples containing Ag, Cu, and ZnO nanoparticles were produced to the same concentrations. Both sample and QC standards were run in the same process (see Table 1) and the results compared.

The ICP-OES analysis was performed on a PerkinElmer Avio 200 ICP-OES with the following conditions as listed in Table 1:

TABLE 1

| ICP-OES Calibration parameters | |
|---|---|
| Plasma gas flow | 10 L/min |
| Auxiliary gas flow | 0.2 L/min |
| Nebulizer gas flow | 0.7 L/min |
| RF power | 1500 watts |
| Pump flow rate | 1.0 mL/min |

The results of the ICP-OES analysis are listed in Table 2:

TABLE 2

ICP-OES Analysis Results

| Element | Units | Untreated Horsehair | Cu 0.5 mg/5 g Treated Horsehair | Cu 20 mg/5 g Treated Horsehair | Ag 0.5 mg/5 g Treated Horsehair | ZnO 0.5 mg/5 g Treated Horsehair | ZnO 20 mg/5 g Treated Horsehair |
|---|---|---|---|---|---|---|---|
| Silver | μg/g | TBD | NR | NR | TBD | NR | NR |
| Copper | μg/g | 5.43 | 16.7 | 735 | NR | NR | NR |
| Zinc | μg/g | 126 | NR | NR | NR | 317 | 1810 |

TBD = to be determined, calibration not yet performed;
NR = No Results

Example 2: Effect of Metallic Nanoparticle-Impregnated Horsehair Brushes on Microbial Growth For each treatment, 5 g of activated horsehairs were treated as above with the following concentrations of metallic nanoparticles:

0.5 mg Silver (Ag)
0.5 mg Copper (Cu)
20 mg Cu
0.5 mg Zinc Oxide (ZnO)
20 mg ZnO Submerged Horsehair Microbial Growth Assays For each sample, 100 mg samples of either untreated horsehair or one of five treated horsehairs (0.5 mg Ag, 0.5 mg Cu, 20 mg Cu, 0.5 mg ZnO, 20 mg ZnO), was disposed into sterile 50 mL conical centrifuge tubes. 5 mL of Nutrient Broth (NB) (Peptone 5 g/L, Beef Extract 3 g/L) was dispensed into each tube and centrifuged at 3000 rpm for 5 min to fully submerge the horsehair.

Microbial strains of *Escherichia coli* (*E. coli*) and *Listeria innocua* Seeliger were purchased from ATCC. Each horsehair suspension was inoculated with either *E. coli* (ATCC® 11229) or *Listeria innocua* Seeliger (ATCC® 33091) to a final concentration of 1,000,000 ($10^6$) colony forming units/mL (CFU/mL). Strains 11229 and 33091 are industry surrogates for strains of food-borne pathogenic *E. coli* or

*Listeria monocytogenes*, respectively. Samples were incubated aerobically at room temperature for 18 hours, followed by measuring optical density (OD) at a wavelength of 600 nm (OD600) to determine bacterial cell density (e.g., OD600 of 1.0=8×$10^8$ cells/mL).

Figure 6:
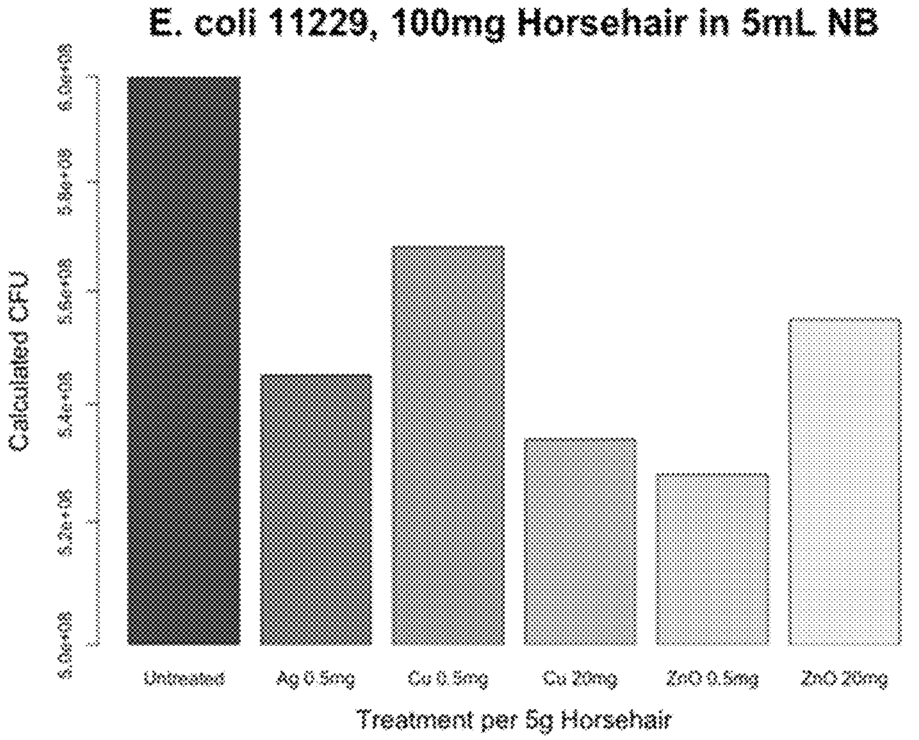
FIG. 6 is a bar chart displaying the results of the growth assay in the presence of horsehair with various treatments.

For *E. coli* 11229, all samples containing treated horsehairs had a lower bacterial cell density than those containing untreated horsehairs (FIG. 6). Reductions in 11229 cell density ranged from 5.5% to 12.1%, with the ZnO 0.5 mg treatment having the greatest reduction.

FIG. 6 is a bar chart displaying the results of the growth assay with *E. coli* 11229 in the presence of horsehair with various treatments. The y-axis is calculated CFU/mL. Treated horsehair samples are listed along the x-axis corresponding to each bar.

All treated horsehairs showed a reduction in bacterial density when compared to an untreated control. Calculated CFU/mL and percent reductions compared to untreated control: Untreated control, 6.01×$10^8$; Ag 0.5 mg, 5.45×$10^8$, 9.3% reduction; Cu 0.5 mg, 5.68×$10^8$, 5.5% reduction; Cu 20 mg, 5.34×$10^8$, 11.1% reduction; ZnO 0.5 mg, 5.28×$10^8$, 12.1% reduction; ZnO 20 mg, 5.55×$10^8$, 7.7% reduction.

Figure 7:
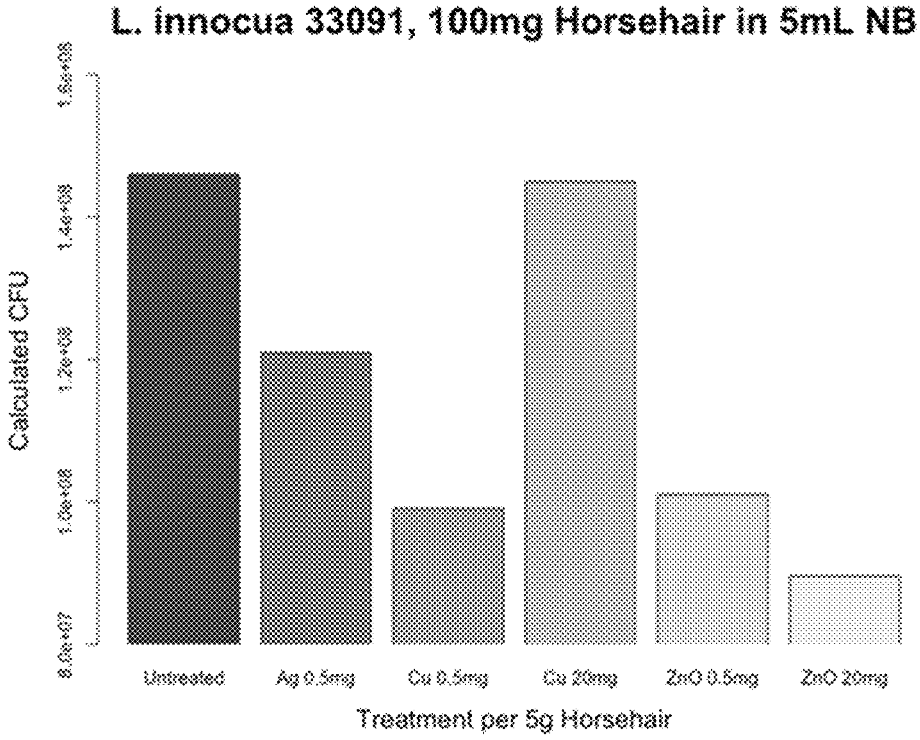
FIG. 7 is a bar chart displaying the results of the growth assay in the presence of horsehair with various treatments.

For *L. innocua* 33091, all samples containing treated horsehairs had a lower bacterial cell density than those containing untreated horsehairs (FIG. 7). Reductions in ATCC® 33091 cell density ranged from 1.1% to 38.8%, with the ZnO 20 mg treatment having the greatest reduction.

FIG. 7 is a bar chart displaying the results of the growth assay with *L. innocua* 33091 in the presence of horsehair with various treatments. The y-axis is calculated CFU/mL. Treated horsehair samples are listed along the x-axis corresponding to each bar.

All treated horsehairs showed a reduction in bacterial density when compared to an untreated control. Calculated CFU/mL and percent reductions compared to untreated control: Untreated control, 1.46×$10^8$; Ag 0.5 mg, 1.21×$10^8$, 17.5% reduction; Cu 0.5 mg, 9.92×$10^7$, 32.2% reduction; Cu 20 mg, 1.45×$10^8$, 1.1% reduction; ZnO 0.5 mg, 1.01×$10^8$, 31.1% reduction; ZnO 20 mg, 8.96×$10^7$, 38.8% reduction.

11229 and 33091 Microbial Attachment CFU Measurement

To determine the density of *E. coli* 11229 or *L. innocua* 33091 attachment following bacterial culture in the presence of ZnO horsehairs and untreated controls, liquid culture was decanted, and inoculated horsehairs were resuspended in 5 mL of Phosphate-buffered saline (PBS) (NaCl 8 g/L, KCl 0.2 g/L, $Na_2HPO_4$ 1.44 g/L, $KH_2PO_4$ 0.24 g/L, $CaCl_2H_2O$ 0.133 g/L, $MgCl_2H_2O$ 0.1 g/L). The suspension was then vortexed at maximum speed for 1 min and the supernatant decanted.

Horsehairs were resuspended in 5 mL of PBS and sonicated for 2 min at a 35 kHz sonication frequency at a temperature of 20° C. in a sonicating water bath, for example, a VWR Scientific Ultrasonic Bath Model 50D. Suspensions were then plated on Nutrient Agar (NA) (Peptone 5 g/L, Beef Extract 3 g/L, Agar, Technical 15 g/L) to determine the number of CFU per 100 mg of inoculated horsehair.

Figure 8:
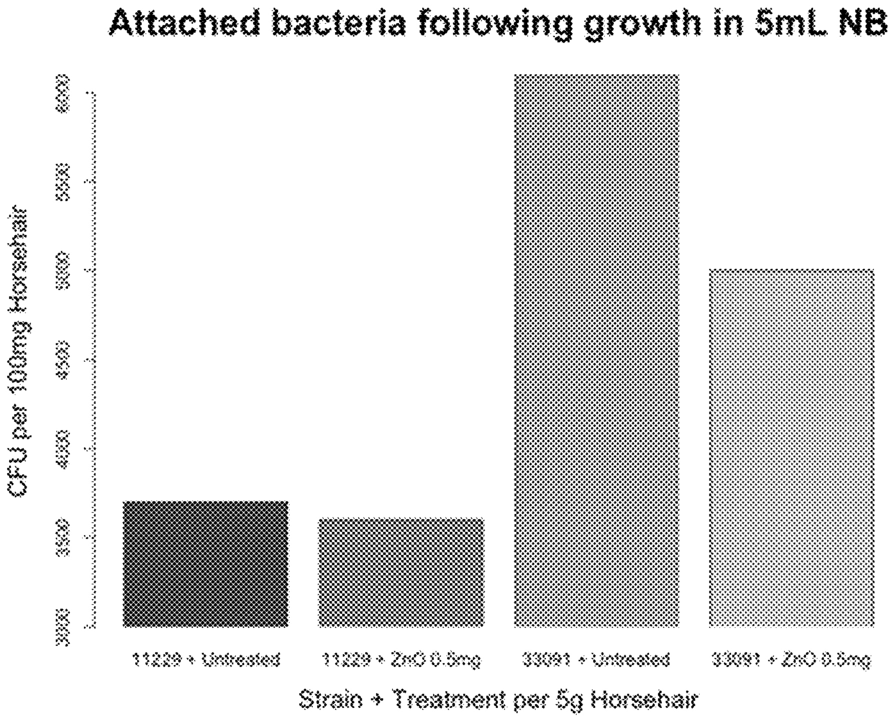
FIG. 8 is a bar chart displaying the results of inoculated horsehairs compared to an untreated control.

For *E. coli* 11229 and *L. innocua* 33091, all samples containing treated horsehairs had fewer bacteria attached than those containing untreated horsehairs as measured by the CFU per 100 mg of inoculated horsehair (FIG. 8). Reductions in 11229 cell density ranged from 5.5-12.1%, with the ZnO 0.5 mg treatment having the greatest reduction. Reductions in 33091 cell density ranged from 1.1-38.8%, with the ZnO 20 mg treatment having the greatest reduction.

FIG. 8 is a bar chart displaying the results of inoculated horsehairs in attached bacteria in NB when compared to an untreated control. The y-axis is CFU per 100 mg of horsehair. Strain and horsehair sample combinations are listed along the x-axis corresponding to each bar. The CFU/mL and corresponding percent reductions compared to untreated controls are as follows: 11229+Untreated horsehair, 3.7×$10^3$; 11229+ZnO 0.5 mg treated horsehair, 3.6×$10^3$, 3% reduction; 33091+Untreated horsehair, 6.1×$10^3$; 33091+ZnO 0.5 mg, 5.0×$10^3$, 18% reduction.

11229 in PBS with OD Measurement

For each sample, 100 mg of either untreated horsehair or one of five treatments (0.5 mg Ag, 0.5 mg Cu, 20 mg Cu, 0.5 mg ZnO, 20 mg ZnO), was disposed into sterile 50 mL conical centrifuge tubes. 5 mL of PBS was dispensed into each tube and centrifuged at 3000 rpm for 5 min to fully submerge the horsehair. Each horsehair suspension was then inoculated with ATCC® 11229 to a final concentration of approximately 6×$10^8$ CFU/mL. Samples were incubated aerobically at room temperature for 18 hours and followed by measuring optical density at a wavelength of 600 nm (OD600) to determine bacterial cell density.

Figure 9:
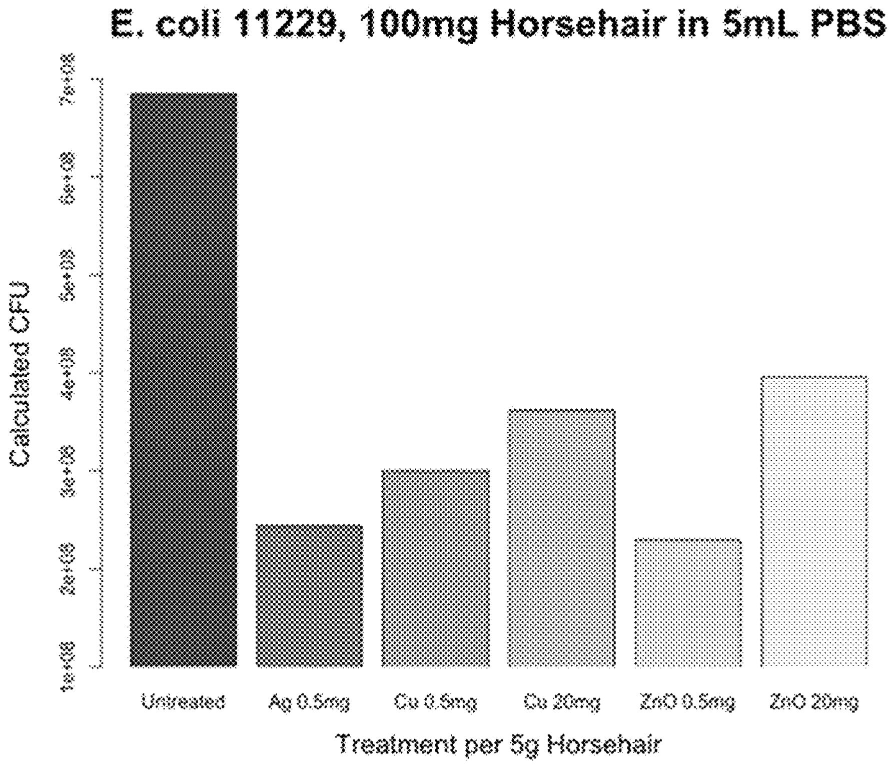
FIG. 9 is a bar chart displaying the results of inoculated horsehairs and attached bacteria when compared to an untreated control.

All samples containing treated horsehairs had a lower *E. coli* 11229 cell density than those containing untreated horsehairs (FIG. 9). Reductions in 11229 cell density ranged from 42-66%, with the Ag 0.5 mg treatment having the greatest reduction.

FIG. 9 is a bar chart displaying the results of *E. coli* 11229 inoculated horsehairs in attached bacteria in PBS when compared to an untreated control. The y-axis is CFU per 100 mg of horsehair. Treated horsehair samples are listed along the x-axis corresponding to each bar.

All treated horsehairs showed a reduction in bacterial density when compared to an untreated control. Calculated CFU/mL and percent reductions compared to untreated control: Untreated control, 6.85×$10^8$; Ag 0.5 mg, 2.44×$10^8$, 64% reduction; Cu 0.5 mg, 3.00×$10^8$, 56% reduction; Cu 20 mg, 3.62×$10^8$, 47% reduction; ZnO 0.5 mg, 2.30×$10^8$, 66% reduction; ZnO 20 mg, 3.96×$10^8$, 42% reduction.

11229 in PBS with CFU Measurement

For each sample, 250 mg of either untreated horsehair or one of five treatments (0.5 mg Ag, 0.5 mg Cu, 20 mg Cu, 0.5 mg ZnO, 20 mg ZnO), was disposed into sterile 50 mL conical centrifuge tubes. 5 mL of PBS was dispensed into each tube and centrifuged at 3000 rpm for 5 min to fully submerge the horsehair. Each horsehair suspension was then inoculated with ATCC® 11229 to a final concentration of approximately 5×$10^7$ CFU/mL. Samples were incubated aerobically at room temperature for 18 hours and then plated on NA to determine bacterial cell density.

Figure 10:
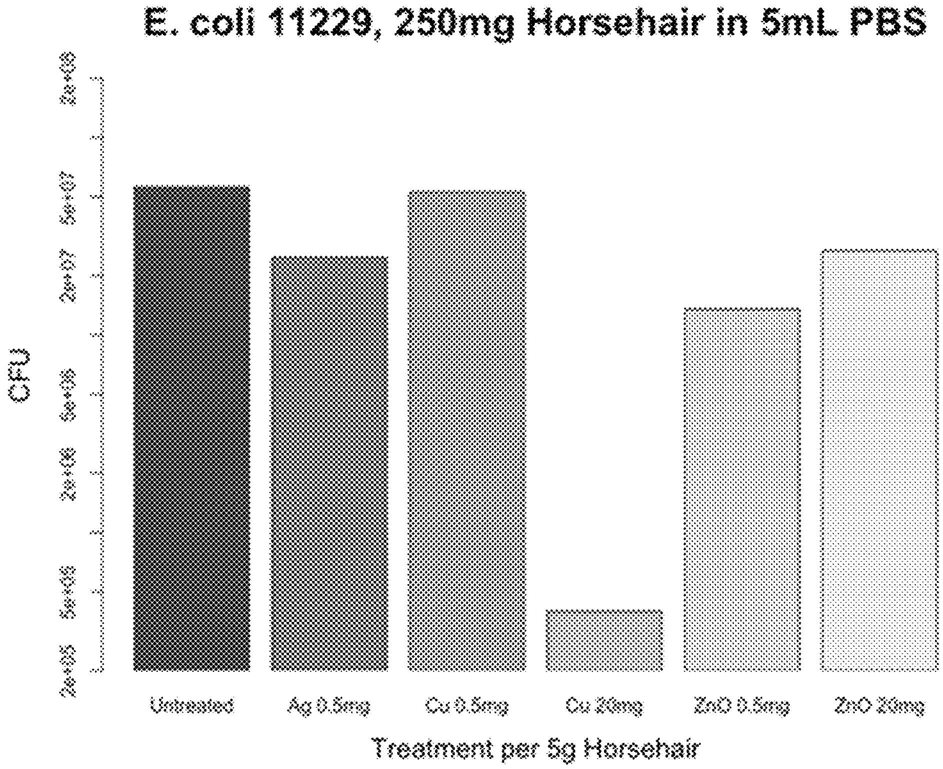
FIG. 10 is a bar chart displaying the results of an incubation assay in the presence of horsehair with various treatments.

All samples containing treated horsehairs had a lower *E. coli* 11229 cell density than those containing untreated horsehairs (FIG. 10). Reductions in 11229 cell density ranged from 5.7-99.3%, with the Cu 20 mg treatment having the greatest reduction.

FIG. 10 is a bar chart displaying the results of the PBS incubation assay with *E. coli* 11229 in the presence of 250 mg of horsehair with various treatments. The y-axis is CFU per 100 mg of horsehair in a logarithmic scale. Treated horsehair samples are listed along the x-axis corresponding to each bar.

All treated horsehairs showed a reduction in bacterial density when compared to an untreated control. CFU/mL and percent reductions compared to untreated control: Untreated control, 5.62×$10^7$; Ag 0.5 mg, 2.48×$10^7$, 55.9% reduction; Cu 0.5 mg, 5.30×$10^7$, 5.7% reduction; Cu 20 mg, 4.00x105, 99.3% reduction; ZnO 0.5 mg, $1.35\times10^7$, 76.0% reduction; ZnO 20 mg, $2.67\times10^7$, 52.5% reduction.

Example 3: Effect of UV Light Exposure on Microbial Growth in Coating Solution

Figure 11:
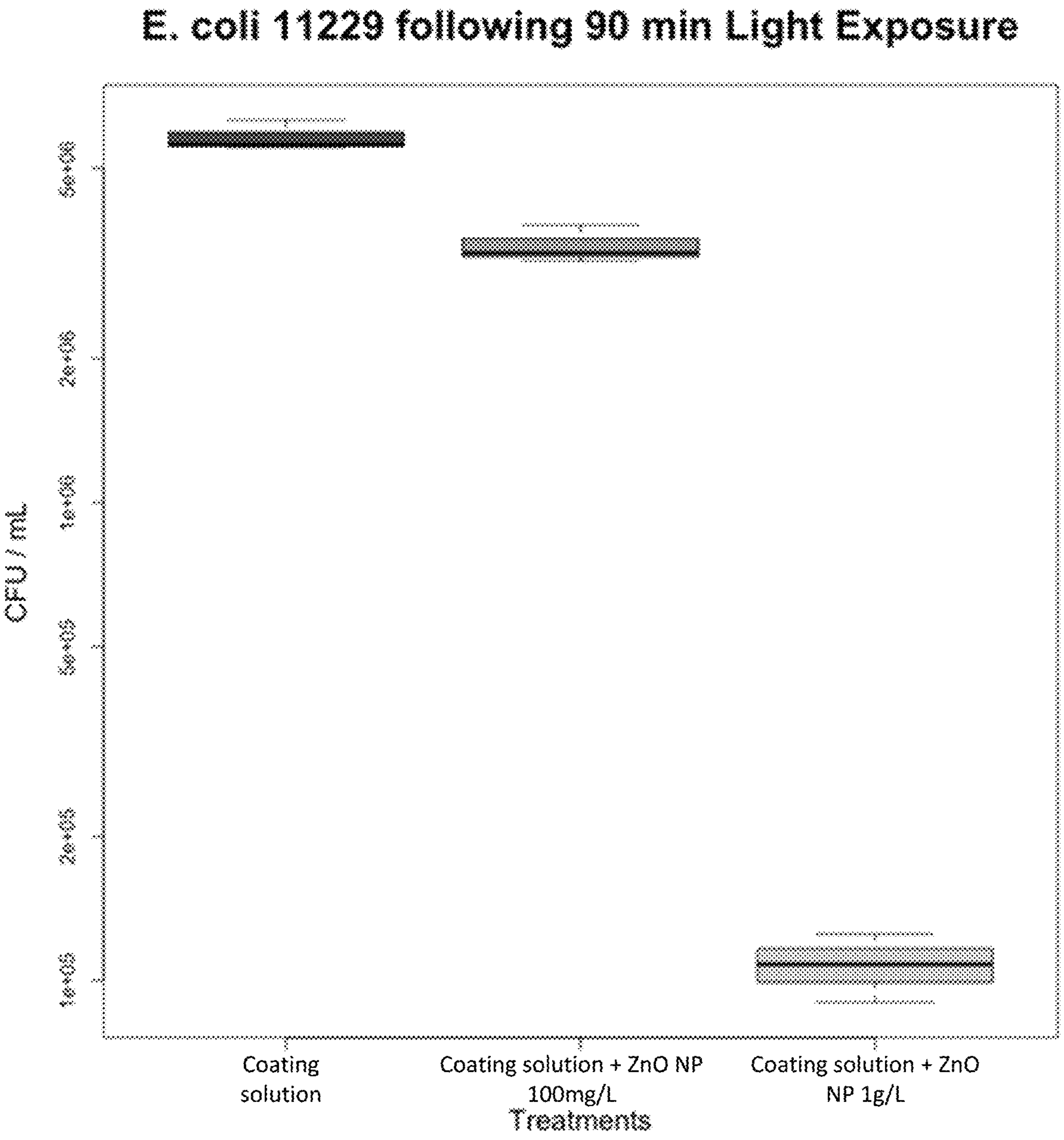
FIG. 11 is a box-and-whisker plot displaying the results of metallic nanoparticle treatment and light exposure on cell density.

Coating Solution and Coating Solution+ZnO 100 mg/L or 1 g/L with CFU Measurement To prepare the three samples, a 25 g/L coating solution of 94% monoglycerides and 6% fatty acids was prepared and allowed to cool to room temperature. For the two treated samples, a ZnO nanoparticle dispersion was added to the coating solution at a concentration of either 100 mg/L or 1 g/L. Each sample was then inoculated with ATCC® 11229 to a final concentration of approximately $5.5\times10^6$ CFU/mL. ZnO-treated samples were exposed to LED lights (having emissions peaks centered on 435 nm and 660 nm) for 90 minutes and then all three samples were plated in triplicate on NA to determine bacterial cell density For both ZnO treated samples, a significant reduction in CFU was observed compared to untreated controls, and ZnO 1 g/L had a significantly lower cell density compared to the other two samples (FIG. 11). ZnO 100 mg/L saw a 39.8% reduction in cell density, and ZnO 1 g/L saw a 98.1% reduction in cell density compared to untreated controls.

FIG. 11 is a box-and-whisker plot displaying the results of the ZnO 1 g/L treatment and either dark, visible light exposure, or long wave UV light exposure on *E. coli* 11229 cell density. The y-axis is CFU/mL of ATCC® 11229 in coating solution on a logarithmic scale. Treatment conditions are listed along the x-axis corresponding to each bar. Light exposed samples had a significant reduction in cell density compared to controls that were maintained in a dark environment, with long wave UV light having the greatest reduction.

Average CFU/mL and percent reduction compared to untreated controls: Dark maintained, $4.80\times10^4$; Visible light exposure, $2.60\times10^3$, 94.6% reduction; Long wave UV light, $1.00\times10^3$, 97.9% reduction.

Coating Solution and Coating Solution+ZnO 1 g/L w/and w/o Light Exposure

To prepare the four samples, a 25 g/L coating solution was prepared and allowed to cool. For the two treated samples, a ZnO nanoparticle dispersion was added to the coating solution at a concentration of 1 g/L. Each sample was then inoculated with *Escherichia coli* ATCC® 11229 for a final concentration of approximately 6.2E6 CFU/mL. One coating solution sample and one ZnO treated sample were exposed to LED grow lights for 90 minutes, while the other two samples were maintained in the dark. Following treatment, all four samples were plated in triplicate on NA to determine bacterial cell density.

Figure 12:
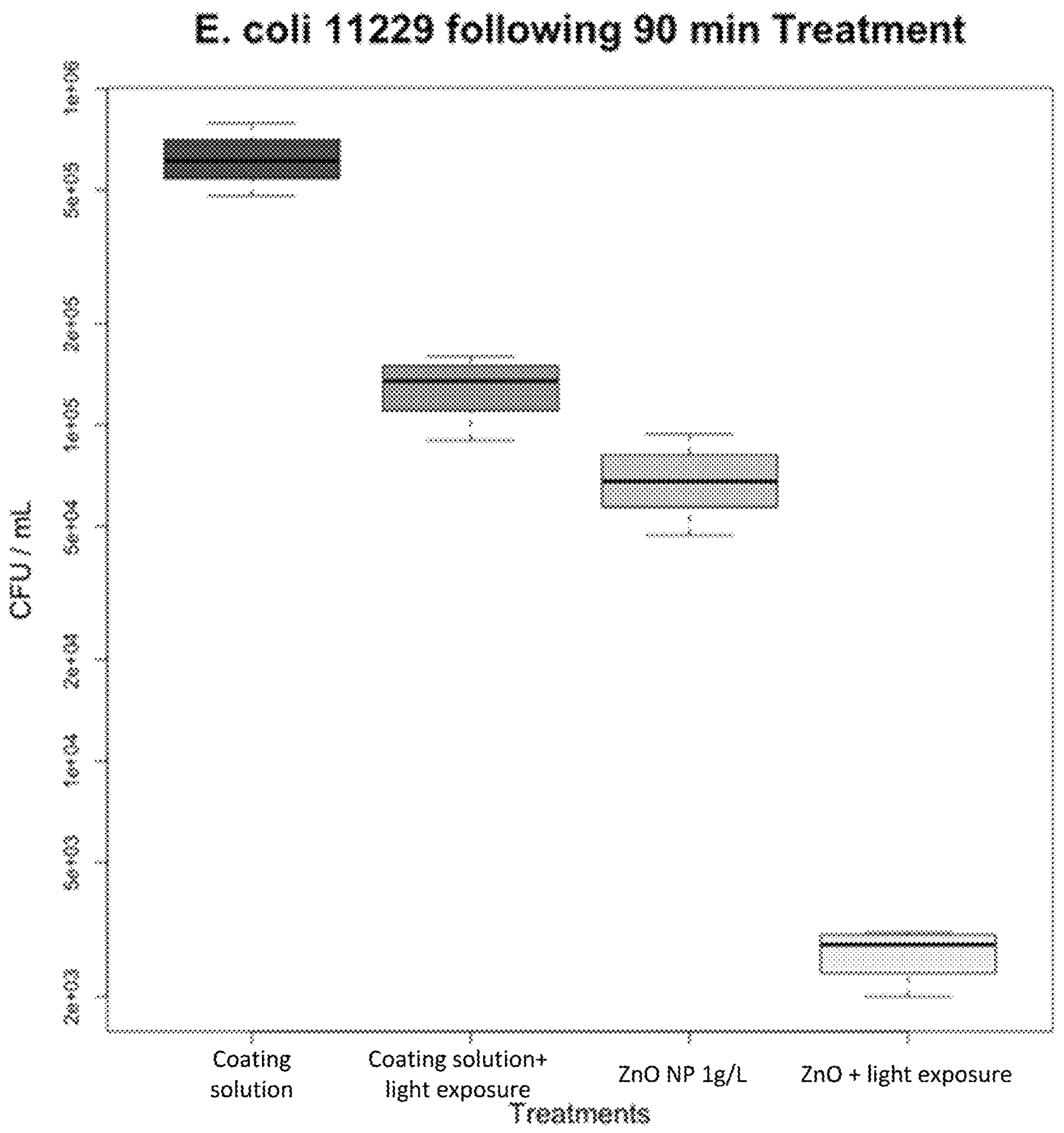
FIG. 12 is a box-and-whisker plot displaying the results of metallic nanoparticle treatment and dark maintenance or light exposure on cell density.

All light exposed and/or ZnO treated samples showed a significant reduction in cell density compared to controls maintained in the dark, and ZnO NP+light exposure treated samples had a significantly lower cell density than all other samples (FIG. 12). Treated samples showed a 79.3-99.6% reduction in cell density, and ZnO 1 g/L with light exposure saw the greatest reduction in cell density.

FIG. 12 is a box-and-whisker plot displaying the results of the ZnO 1 g/L treatment and dark maintenance or light exposure on *E. coli* 11229 cell density. The y-axis is CFU/mL of ATCC® 11229 in a coating solution on a logarithmic scale. Treatment conditions are listed along the x-axis corresponding to each bar.

All light exposed and/or ZnO treated samples showed a significant reduction in cell density compared to controls maintained in the dark, and ZnO NP+light exposure treated samples had a significantly lower cell density than all other samples. Average CFU/mL and percent reduction compared to untreated controls: coating solution 25 g/L, $6.23\times10^5$; coating solution+90 min light exposure, $1.29\times10^5$, 79.3% reduction; coating solution+ZnO NP 1 g/L, $6.93\times10^4$, 88.9% reduction; coating solution+ZnO NP 1 g/L+90 min light exposure, $2.70\times10^3$, 99.6% reduction.

Coating Solution+ZnO 1 g/L in Dark, Visible Light, or Long Wave UV Light

To prepare the three samples, a 25 g/L coating solution was prepared and allowed to cool. A ZnO nanoparticle dispersion was added to the coating solution at a concentration of 1 g/L. Each sample was inoculated with *Escherichia coli* ATCC® 11229 for a final concentration of approximately $6.0\times10^5$ CFU/mL. Samples were then either maintained in the dark, exposed to LED grow lights (wavelengths described above), or exposed to long wave UV light for 90 minutes. Following treatment, all three samples were plated in triplicate on NA to determine bacterial cell density.

Figure 13:
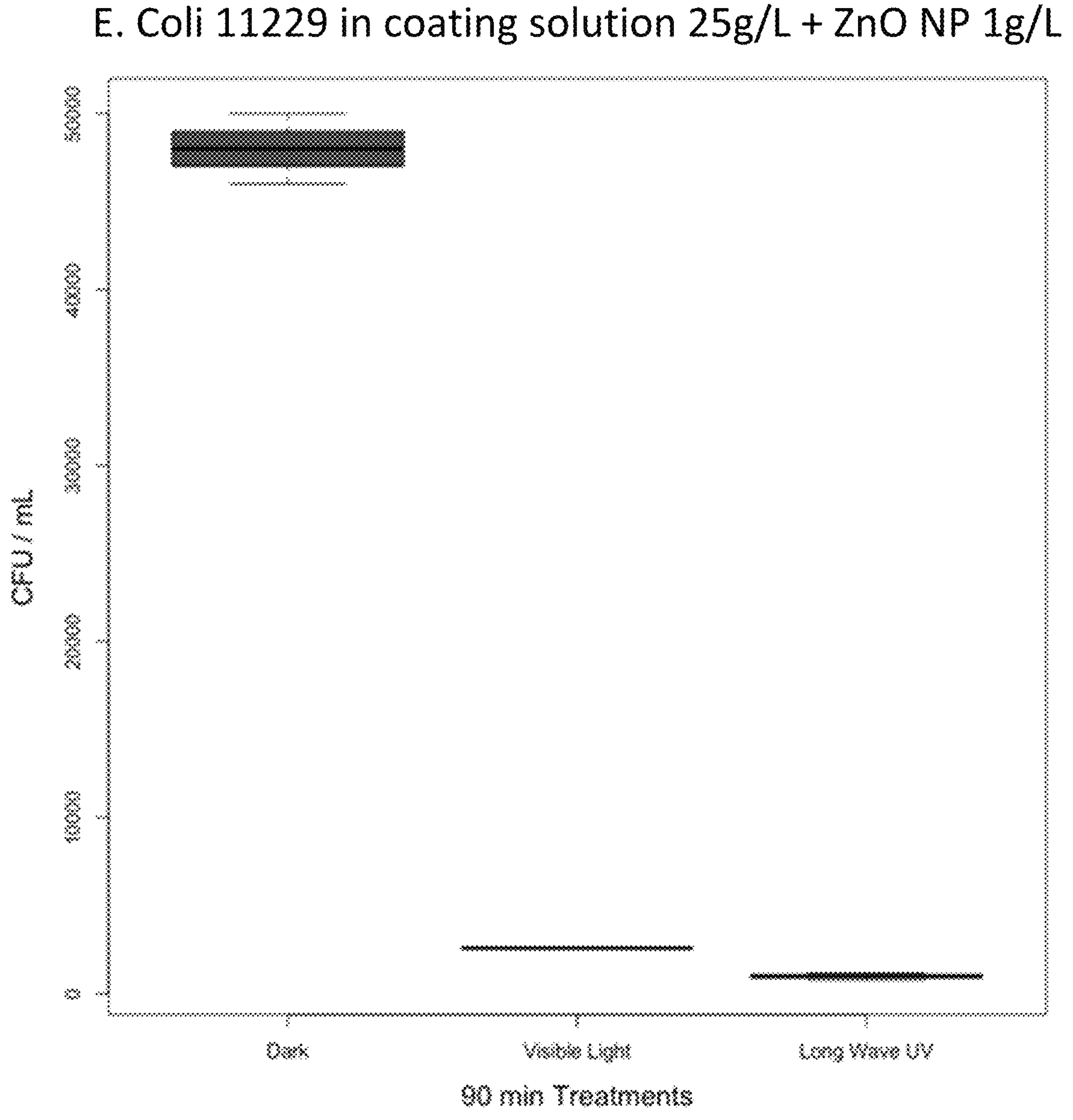
FIG. 13 is a box-and-whisker plot displaying the results of metallic nanoparticle treatment and light exposure on cell density.

For both light exposed samples, a significant reduction in CFU was observed compared to controls that were maintained in the dark (FIG. 13). Samples exposed to visible light showed a 94.6% reduction in cell density, and those exposed to long wave UV light a 97.9% reduction in cell density.

FIG. 13 is a box-and-whisker plot displaying the results of the ZnO 1 g/L treatment and either dark, visible light exposure, or long wave UV light exposure on *E. coli* 11229 cell density. The y-axis is CFU/mL of ATCC® 11229 in a coating solution at 25 g/L. Treatment conditions are listed along the x-axis corresponding to each bar.

All light exposed and/or ZnO treated samples showed a significant reduction in cell density compared to controls maintained in the dark, and ZnO NP+light exposure treated samples had a significantly lower cell density than all other samples. Average CFU/mL and percent reduction compared to untreated controls: coating solution 25 g/L, $6.23\times10^5$; coating solution+90 min light exposure, $1.29\times10^5$, 79.3% reduction; coating solution+ZnO NP 1 g/L, $6.93\times10^4$, 88.9% reduction; coating solution+ZnO NP 1 g/L+90 min light exposure, $2.70\times10^3$, 99.6% reduction.

Example 4: Effect of Thin Film UV Light Reactor on Microbial Load

Figure 14:
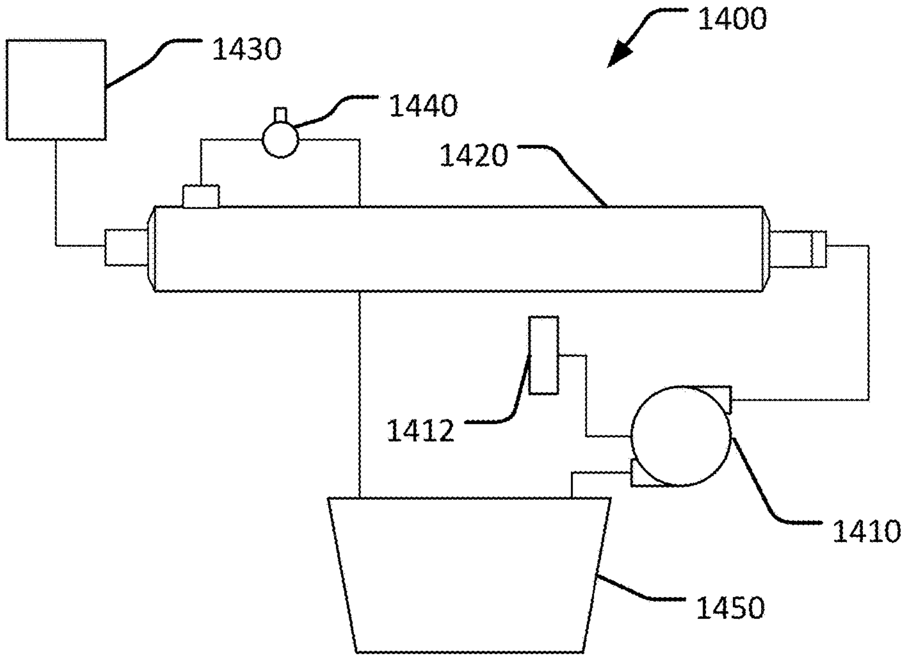
FIG. 14 schematically illustrates an example recirculation loop including UV light reactor.

FIG. 14 schematically depicts testing equipment 1400 for applying UV light to a volume of coating mixture inoculated with microbial load. The testing equipment 1400 includes an air-operated diaphragm pump 1410 capable of pumping liquid through the equipment 1400 in fluidic communication with a pressure regulator 1412 and an on/off valve to control the start, stoppage, and flow rate of coating mixture. The testing equipment 1400 further includes a UV reactor 1420. The reactor 1420 encases a high-output, low-pressure mercury lamp housed inside a quartz sleeve. The quartz sleeve filters light emitted from the lamp such that only UV light between 240 nm and 260 nm (e.g., 254 nm) is emitted from the sleeve. The lamp is operated by a controller box 1430 mounted to the test cart. The testing equipment 1400 also includes a sample valve 1440 connected to the outlet of the UV reactor and a reservoir 1450 of coating mixture to be treated.

Parameters of the lamp within the reactor 1420 are noted in Table 1.

TABLE 1

| | |
|---|---|
| Reactor Length | 145 cm |
| Lamp Sleeve Diameter | 2.5 cm |
| Reactor Inside Diameter | 3.8 cm |
| Reactor Volume | 0.92 Liters |
| Lamp Power | 135 Watts |
| Lamp Efficiency | 40% |
| Pump Flow Rate | 2.5 gal/min |
| Estimated UV Flux | ~22 mW/cm$^2$ |
| Estimated UV Dose | ~56 mJ/cm$^2$ |

Treatment of Coating Mixture

The reservoir 1450 is filled with 10 L of coating mixture carrying a suspended 50 g/L coating solution and dosed with 10 mL~$10^9$ CFU/mL suspension of *Listeria innocua* Seeliger 51742 (ATCC® 51742).

The reservoir 1450 is connected to the diaphragm pump which is operated at a 2.5 gal/min flow rate to distribute the inoculated liquid coating mixture through the treatment loop and mix the coating solutions and ATCC® 51742 solution. The diaphragm pump is operated for two minutes to ensure even distribution of bacteria.

The UV lamp within the reactor 1420 is turned on and a run timer is initiated coincidentally.

Samples of the mixture are collected from the sampling valve 1440 at predetermined time intervals and the absorbance measured to determine the microbial load remaining in solution.

The method was run for two trials, and samples from each were analyzed to determine the remaining CFU/mL of ATCC® 51742. Table 2 shows a summary of time versus survivor population (A), and the corresponding log scale values. The first column of Table 2 denotes to which trial the underlying rows of data correspond; the second column indicates the time in minutes at which the sample was removed from the sampling valve 1440; the third column indicates the estimated survivor population (A); and the fourth column indicates the base 10 logarithm value of the estimated survivor population (A) and provide the charted values of FIG. 15. For reference, the experimental limit of detection corresponds with a log A value of 1.7 (e.g., ~50 CFU/mL).

TABLE 2

| | Time (min) | A CFU/ml | log A |
|---|---|---|---|
| Run 1 | 0 | 1750000 | 6.24 |
| | 2 | 15000 | 4.18 |
| | 3 | 6000 | 3.78 |
| | 4 | 3000 | 3.48 |
| | 5 | 750 | 2.88 |
| | 10 | 0 | 1.70 |
| | 15 | 50 | 1.70 |
| | 20 | 25 | 1.70 |
| Run 2 | 0 | 1750000 | 6.24 |
| | 3 | 27500 | 4.44 |
| | 5 | 1500 | 3.18 |
| | 7 | 500 | 2.70 |
| | 8 | 100 | 2.00 |
| | 11 | 200 | 2.30 |
| | 21 | 50 | 1.70 |

Figure 15:
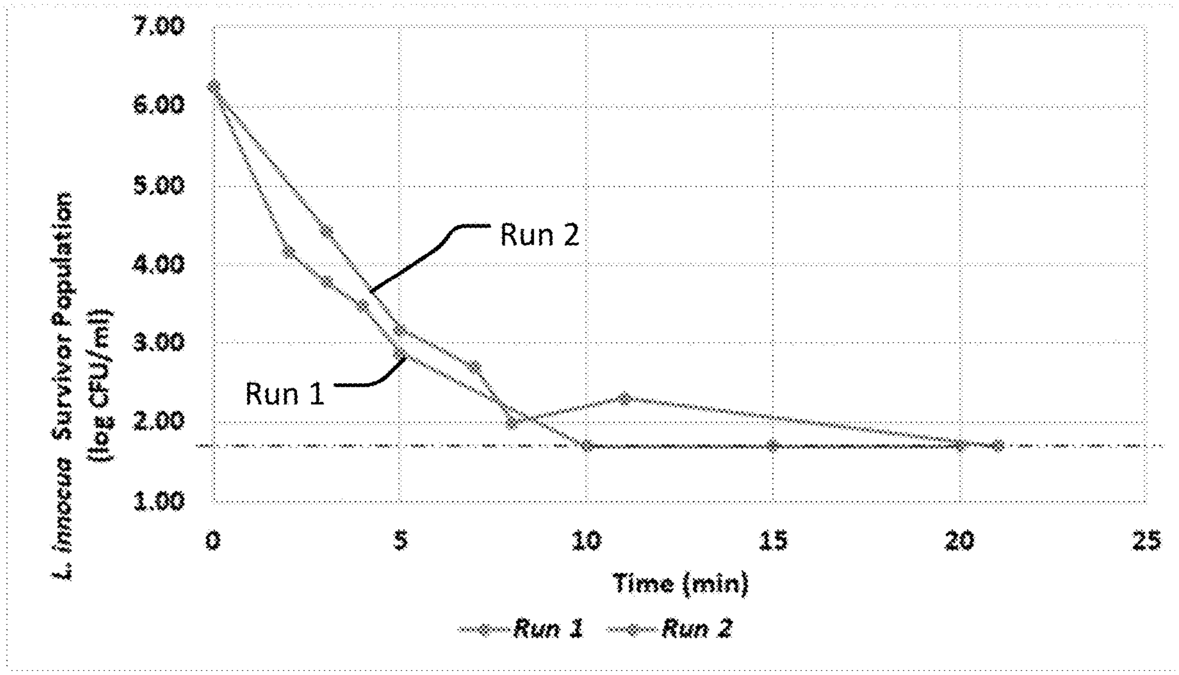
FIG. 15 is a line graph comparing time to the logarithmic value of the estimated survivor population.

FIG. 15 is a line graph depicting the connected data of Table 2 comparing experiment total time (minutes) along the x-axis to the logarithmic value of the estimated ATCC® 51742 survivor population (log CFU/mL). Run 1 and Run 2 are shown approximately following the same declining ATCC® 51742 survivor population curve as the coating mixtures spends increasing time within the testing equipment 1400. The limit of detection is shown as a dashed line parallel with the x-axis at approximately 1.7 units. The terminal three time points of Run 1 are shown on the limit of detection line.

Based on an estimated reactor volume of 0.918 L, and a flow rate through the pressure regulator of 0.158 L/s (2.5 gal/min), the entire initial volume of inoculated coating mixture passes through the testing equipment 1400 in 63.5 seconds, with an average residence time of 5.8 seconds within the reactor 1420. The relationship between average residence time and surviving population is shown in FIG. 16.

Figure 16:
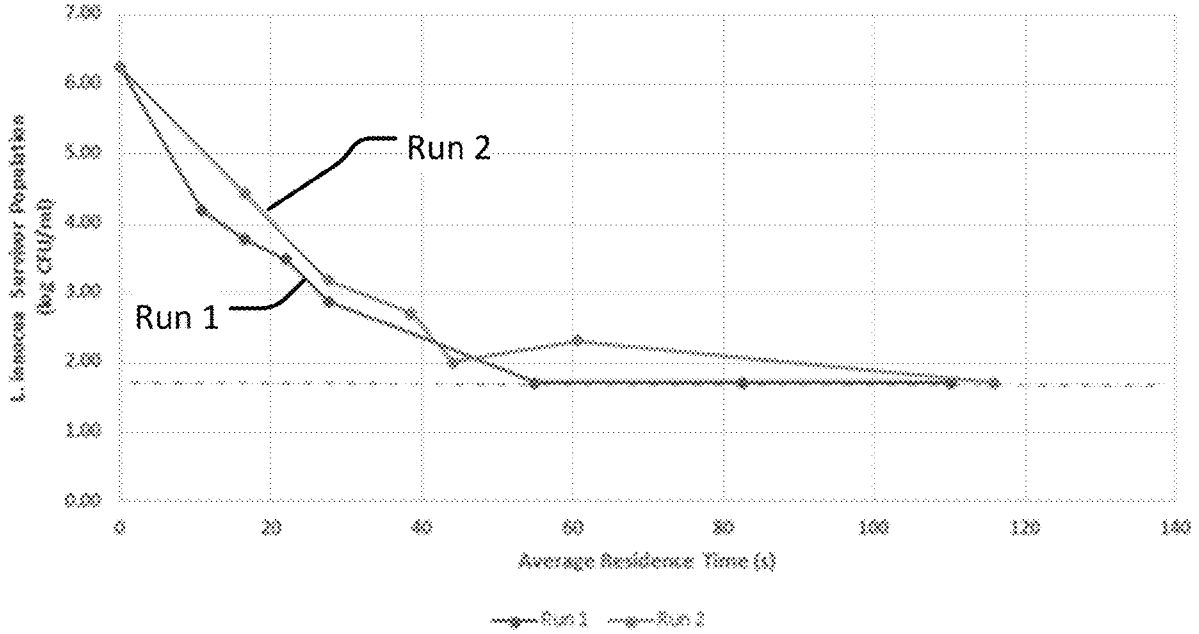
FIG. 16 is a line graph comparing average residence time to the logarithmic value of the estimated survivor population.

FIG. 16 is a line graph depicting the connected data of Table 2 comparing average residence time (s) along the x-axis to the logarithmic value of the estimated ATCC® 51742 survivor population (log CFU/mL). The x-axis value is calculated by multiplying the theoretical number of passes of the entire initial volume by the residence time (e.g., volume of reactor/flow rate) which amounts to average amount of time any amount of liquid has spent inside the reactor. For example, the initial volume takes approximately 4 minutes to reach 4 theoretical passes through the system, which corresponds to 22 seconds of average residence time for the entire liquid volume.

Run 1 and Run 2 are shown approximately following the same declining ATCC® 51742 survivor population curve as collected samples spend increasing residence time circulating within the testing equipment 1400. The limit of detection is shown as a dashed line parallel with the x-axis at approximately 1.7 units.

The testing equipment 1400 reduced the population of ATCC® 51742 to limit-of-detection levels in both trials. There was an average reduction of 2.60 log values from initial bacterial concentrations (e.g., 6.24 log values at t=0) after ~4 estimated passes (e.g., 4 minutes and 22 seconds average residence time). The reduction after ~8 passes was 4.16 log values from initial bacterial concentrations (e.g., 6.24 log values at t=0).

The estimated dose for this flow rate and assuming a ~6% UV transmittance liquid is ~56 mJ/cm^2. This value does not take into account the change in solution turbidity due to bacterial inoculation, and potential variation in the UV transmittance of coating solution solutions.

Example 5: Effect of Metallic Nanoparticle Impregnated Polymers on Microbial Growth Submerged Polymer Growth Assays Each polymer tube (Table 3) was cut into ring samples of a width between 1 mm and 2 mm such that each sample weighed 2.15 g. Each sample was added into separate sterile 50 mL conical centrifuge tubes. 5 mL of PBS was dispensed into each tube containing a polymer sample as well as a control tube containing no polymer sample. Each tube containing a polymer sample was then inoculated with *E. coli* 11229 for a final concentration of approximately $2\times10^5$ CFU/mL. Samples were incubated aerobically at 30° C. for 18 hours and then plated on NA to determine bacterial cell density.

TABLE 3

| Polymer samples. |
|---|
| Brewmaster Ultra Barrier Silver ™ Anti-Bacterial Beer Tubing, ½" inner diameter |
| Saint-Gobain Versilon ™ Silver Antimicrobial, Flexible Tubing |
| United States Plastic Corp. CLEARFLO ® Ag-47 Clear Antimicrobial PVC Tubing |

Figure 17:
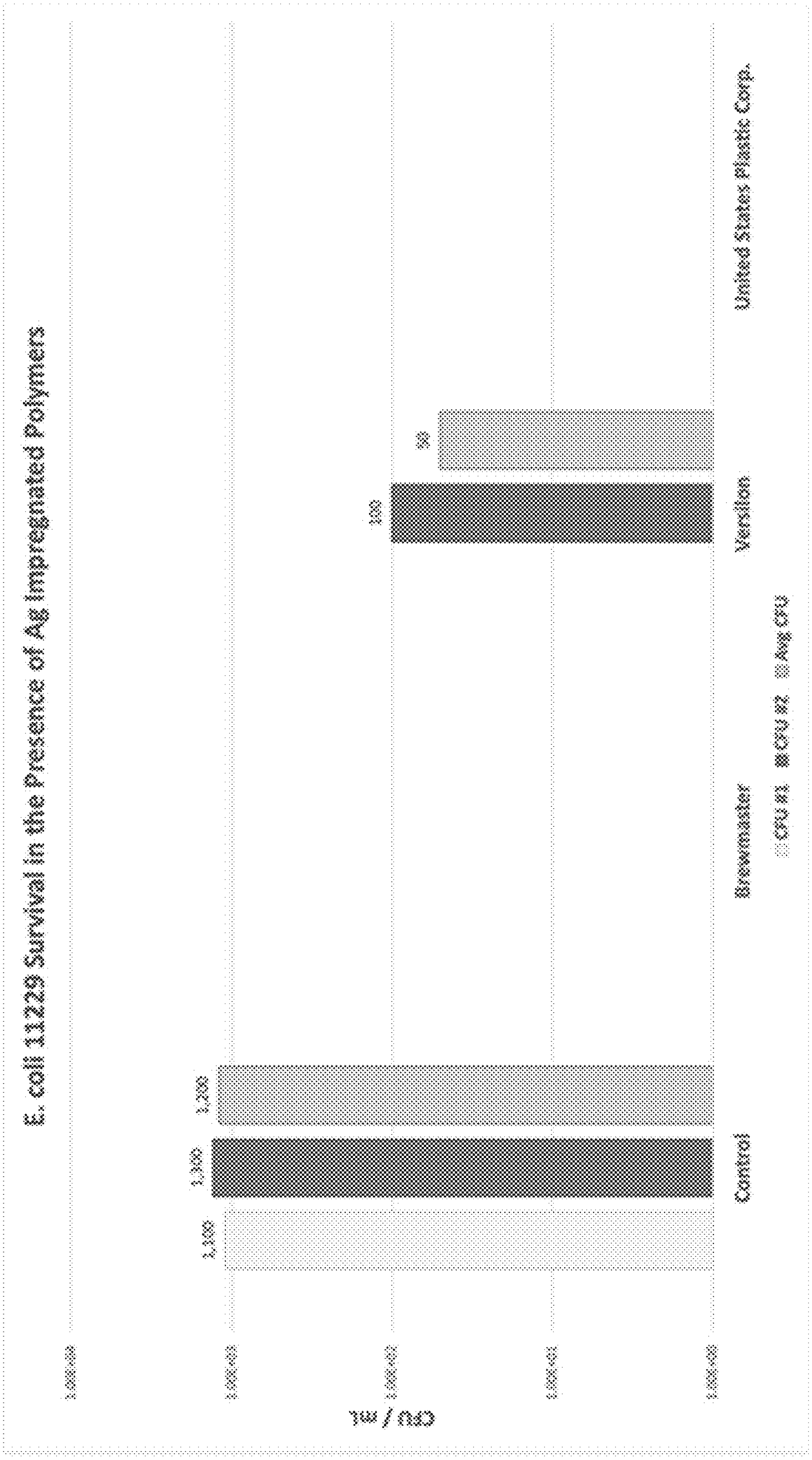
FIG. 17 is a bar chart displaying the results of metallic nanoparticle treatment in various polymers.

FIG. 17 is a bar chart displaying the results of the growth assay with *E. coli* 11229 in the presence of various polymer samples. The y-axis is a calculated CFU per mL of inoculated PBS suspension on a logarithmic scale. Polymer samples labels are listed along the x-axis beneath each bar corresponding to the samples of Table 3 and the control tube described above, labeled 'Control'. The bars are shaded to correspond with CFU measurement replicates, the right light grey bar of each sample being the first replicate, the second dark grey bar being the second replicate, and the left bar grey bar being the average of the first and second replicates. A key is shown beneath the x-axis.

For example, the Versilon sample bars depict a first replicate (not shown) CFU measurement of 1×10° CFU/mL (1) and the second replicate (dark grey bar) CFU measurement of $1\times10^2$ CFU/mL (100), the average (right bar) of the first and second being $5\times10^1$ CFU/mL (50).

All samples containing polymers samples had a lower *E. coli* 11229 cell density than those containing only PBS (Control columns of FIG. 17). The reductions in *E. coli* 11229 cell density is 95.8% or more, with no viable cells detected in both the Brewmaster polymer suspended sample or the United States Plastic Corp. suspended sample (detection limit $1\times10^2$ CGU/mL).

What is claimed is:

1. A method for treating a product, comprising:
removing a plurality of particulates from a surface of a product;
exposing the surface of the product to a light of a first wavelength;
heating a coating mixture to a first temperature; and
coating the product with the heated coating mixture.

2. The method of claim 1, wherein removing the plurality of particulates comprises brushing the surface of the product with an antimicrobial brush which includes an antimicrobial compound selected from a group consisting of a nanoparticle, an antibiotic compound, and an oxide.

3. The method of claim 1, comprising, after heating the coating mixture to the first temperature, cooling the coating mixture to a second temperature before coating the product with the heated coating mixture.

4. The method of claim 1, wherein the first wavelength is between 200 nm and 280 nm.

5. The method of claim 1, wherein the coating mixture includes an antimicrobial compound activated by exposure to ultraviolet radiation of a first wavelength.

6. The method of claim 5, wherein the method further comprises exposing, following coating, the product to a light of the first wavelength.

7. The method of claim 6, wherein the first wavelength is in range from 200 nm and 280 nm.

8. The method of claim 6, wherein the exposing comprises exposing the product to the light of the first wavelength such that the coating mixture receives an estimated dose threshold of at least 5 $mWs/cm^3$.

9. The method of claim 8, wherein the estimated dose threshold is at least 10 $mWs/cm^3$.

10. The method of claim 9, wherein the coating comprises spraying, via a plurality of sprayers, the coating mixture onto the product at a flow rate sufficient such that the coating mixture receives the estimated dose threshold.

11. The method of claim 1, wherein the coating comprises coating the product with the heated coating mixture using antimicrobial brushes.

12. The method of claim 3, wherein the first temperature is in a range from 75° C. and 100° C., and the second temperature is in a range from 50° C. and 90° C.

13. The method of claim 12, comprising mixing a coating agent in a solvent to form the coating mixture.

14. The method of claim 13, wherein the mixing further comprises mixing a sanitizing agent with the coating agent in the solvent.

15. The method of claim 13, wherein the mixing further comprises mixing an antimicrobial compound with the coating agent in the solvent.

16. The method of claim 15, wherein the antimicrobial compound is a nanoparticle comprising a metallic compound.

* * * * *